(12) United States Patent
Milton

(10) Patent No.: US 11,865,027 B1
(45) Date of Patent: Jan. 9, 2024

(54) HAMSTRING SUPPORT SYSTEM AND METHOD OF USE

(71) Applicant: Matthew Danzel Milton, Plantation, FL (US)

(72) Inventor: Matthew Danzel Milton, Plantation, FL (US)

(\*) Notice: Subject to any disclaimer, the term of this patent is extended or adjusted under 35 U.S.C. 154(b) by 413 days.

(21) Appl. No.: 17/073,383

(22) Filed: Oct. 18, 2020

Related U.S. Application Data

(60) Provisional application No. 62/973,667, filed on Oct. 18, 2019.

(51) Int. Cl.
*A61F 5/37* (2006.01)
*A61F 5/01* (2006.01)

(52) U.S. Cl.
CPC .......... *A61F 5/3715* (2013.01); *A61F 5/0104* (2013.01); *A61F 2005/0197* (2013.01)

(58) Field of Classification Search
CPC ........ A61F 5/0104; A61F 5/37; A61F 5/3715; A61F 2005/0197; A61H 1/02; A61H 1/0237; A63B 21/00061; A63B 21/00185; A63B 21/02; A63B 21/04; A63B 21/055; A63B 21/0552; A63B 21/4009; A63B 21/4011; A63B 21/4015; A63B 21/4023; A63B 21/4025; A63B 23/03508; A63B 69/0028
See application file for complete search history.

(56) References Cited

U.S. PATENT DOCUMENTS

| | | | | |
|---|---|---|---|---|
| 4,166,460 A | * | 9/1979 | Applegate | A61F 5/0111 602/65 |
| 4,865,023 A | * | 9/1989 | Craythorne | A61F 5/0111 602/27 |
| 5,316,545 A | * | 5/1994 | Cherubini | A43B 7/1464 264/222 |
| 5,716,307 A | * | 2/1998 | Vadher | A63B 21/4043 482/125 |
| 6,428,495 B1 | * | 8/2002 | Lynott | A61F 5/3715 602/23 |
| 6,837,862 B2 | * | 1/2005 | Driver, Jr. | A61F 5/3715 128/882 |
| 7,261,679 B2 | * | 8/2007 | Sload | A63B 69/0059 482/79 |
| 9,186,536 B2 | * | 11/2015 | Strachan | A63B 21/0557 |
| 10,245,459 B1 | * | 4/2019 | Cranke | A63B 21/00061 |
| 10,843,332 B2 | * | 11/2020 | Walsh | B25J 9/1694 |
| 10,926,124 B2 | * | 2/2021 | Marti | A61H 1/0266 |
| 11,241,340 B2 | * | 2/2022 | Allen | A61F 13/06 |

(Continued)

*Primary Examiner* — Keri J Nelson
(74) *Attorney, Agent, or Firm* — Allen D. Hertz, P.A.; Allen D. Hertz

(57) ABSTRACT

A hamstring support system comprising a waist strap, a heel cup and an elongated biasing element assembly elastically extending between the waist strap the heel cup. The waist strap is secured to a waistline of a patient having an injured or recovering hamstring injury. The heel cup is secured to a heel of an injured leg of the patient. A length of the biasing element assembly is adjusted to a neutral or slight biasing force when the injured leg is bent, thus providing a supporting force when the injured leg is extended. A pliant material can be placed between the heel cup and the heel. A shoe is preferably worn over the heel cup.

20 Claims, 12 Drawing Sheets

(56) References Cited

U.S. PATENT DOCUMENTS

| | | | |
|---|---|---|---|
| 2006/0009725 A1* | 1/2006 | Lampkins | A61F 5/0111 602/5 |
| 2010/0041527 A1* | 2/2010 | Miller | A63B 21/4007 206/223 |
| 2019/0240057 A1* | 8/2019 | Gunnsteinsson | A61F 5/0111 |

* cited by examiner

HAMSTRING SUPPORT SYSTEM AND METHOD OF USE

CROSS REFERENCE TO RELATED APPLICATIONS

This application is a Non-Provisional Utility Applications claiming the benefit of U.S. Provisional Patent Application Ser. No. 62/973,667, filed on Oct. 18, 2019, which is incorporated by reference herein in its entirety.

FIELD OF THE INVENTION

The general invention is directed towards a hamstring supporting device and an associated method of use. More specifically, a hamstring supporting device comprising a waist strap, a heel cup, and an elongated biasing element spanning between the waist strap and the heel cup. In use, the heel cup is placed on a heel of a leg having an injured or recovering hamstring, the waist strap is secured about the patient's waistline, and the elongated biasing element assembled having a first portion secured to the waist strap and a second portion secured to the heel cup. A shoe is preferably placed over the patient's foot wearing the heel cup.

BACKGROUND OF THE INVENTION

Hamstring injuries can dampen a sports player's abilities. Additionally, hamstring injuries can be aggravated during practice and/or play of a respective sports game. When a sports player injures their hamstring, it is commonplace to undergo rehabilitation and recovery prior to returning to play of any particular sports game. The span of time during rehabilitation and recovery impacts both the player and the team.

There are three (3) muscles that make up the hamstring muscle group. The three (3) muscles that make up the hamstring muscle group include the semitendinosus, the semimembranosus, and the biceps femoris.

The three (3) muscles that make up the hamstring muscle group have a common proximal attachment on the posterior side of the ischial tuberosity. Distally, they attach to the tibia and the fibula. More specifically, the semitendinosus attaches medially at the pes *anserinus* site on the medial tibia; the flat conjoined tendons of the sartorius, gracilis and semitendinosus collectively reinforce the posterior medial capsule. The semimembranosus tendon attaches to the posterior medial condyle of the tibia, but also has fibrous extensions that blend with the posterior capsule of the knee. Semimembranosus also has an attachment to the medial meniscus. Lastly, the biceps femoris attaches on the posterior superior aspect of the proximal fibular head.

Due to the proximal attachments crossing the hip joint posteriorly, and the distal attachments crossing the knee joint posteriorly, this muscle is considered a bi-articular muscle. Thus, the hamstring is responsible for extension at the hip joint and flexion at action at the knee joint.

While walking, stretching, jogging, or cycling, forces are developed more slowly and in a repetitive or cyclic fashion. In these examples, the length changes in the rectus femoris (quadricep) and semitendinosus (hamstring) are relatively small throughout much of the activation cycle. Therefore, the hamstring muscle avoids repetitive cycles of storing and immediately releasing relatively large amounts of energy, but rather more moderate levels of active and passive forces are cooperatively shared between muscles, thereby optimizing the metabolic efficiency of the movement.

During the running gait cycle, with respect to the front leg, we can observe a motion of hip flexion and knee extension simultaneously occurring (actions directly opposite to those responsible of the hamstring as previously mentioned, hip extension and knee flexion). To move the leg through this motion, what can be observed is a rapid and near-full contraction of the rectus femoris to simultaneously flex the hip and extend the knee. This powerful motion is fueled by elastic energy that is stored in the stretched rectus femoris when the leg is in the back-leg position of the running cycle, where a combined hip extension and knee flexion motion has occurred.

As the leg rapidly moves forward into this front leg position of the stride, the bi-articular hamstrings are overstretched across both the hip and knee joint, as a means of passively resisting hip flexion and knee extension. This is the position in which the hamstring is most often injured.

What is desired is an apparatus that bridges a gap between rehabilitation and returning to practice and play of a respective sports game.

SUMMARY OF THE INVENTION

The present invention overcomes the deficiencies of the known art by introducing a hamstring support assembly comprising an elongated biasing element having a first distal location secured to a waist strap and a second, opposite distal location secured to a heel cup.

In accordance with one embodiment of the present invention, the invention includes a hamstring support assembly, comprising:
   the waist band;
   a heel cup comprising a sole panel and a heel panel; and
   an elongated biasing element extending between the waist band and the heel cup.

In a second aspect, the elongated biasing element is adjustable in length.

In yet another aspect, the elongated biasing element further comprising a length adjustment mechanism.

In yet another aspect, the elongated biasing element further comprising a length adjustment mechanism, wherein the length adjustment mechanism additionally aids in attachment of the elongated biasing element to the heel cup.

In yet another aspect, the elongated biasing element further comprising a length adjustment mechanism, wherein the length adjustment mechanism additionally aids in attachment of the elongated biasing element to the waist strap.

In another aspect, the sole of the heel cup has a width that is substantially equal to a width of a foot of a patient.

In yet another aspect, the heel cup can further include a heel cup comprising a sole panel a heel panel, and an arched transition between the sole panel the heel panel.

In another aspect, the heel cup is formed defining a heel receiving cavity; the heel receiving cavity is shaped to follow a contour of the patient's foot.

In yet another aspect, the sole panel having an arched shape, the arched shape being concave on an interior surface.

In yet another aspect, the sole panel having a multi-curved shape, the multi-curved shape being concave on lower portion of an interior surface and convex on an upper portion of the interior surface.

In yet another aspect, the heel cup can further include a right side panel and a left side panel.

In yet another aspect, the heel cup can further include a right side panel and a left side panel, the right side panel having an arched shape, the arched shape being concave on an interior surface, the left side panel having an arched shape, the arched shape being concave on an interior surface.

In yet another aspect, the heel cup can further include a right side panel and a left side panel, the right side panel having an upper edge extending between an upper, right edge of the heel panel and a forward, right edge of the sole panel and the left side panel having an upper edge extending between an upper, left edge of the heel panel and a forward, left edge of the sole panel.

In another aspect, the heel cup can further include an arched transition between the sole panel the heel panel.

In another aspect, the heel cup can further include a first arched transition provided between the heel panel and the right side panel and a second arched transition provided between the heel panel and a left side panel.

In yet another aspect, the heel cup can further include a right side panel extending upward from a right edge of the heel cup and a left side panel extending upward from a left edge of the heel cup.

In yet another aspect, the heel cup can further include a biasing element attachment feature.

In yet another aspect, the heel cup can further include a biasing element attachment feature, the biasing element attachment feature being provided in a form of a biasing element receiving aperture.

In yet another aspect, the heel cup can further include a biasing element receiving aperture.

In yet another aspect, the heel cup can further include a biasing element receiving aperture, the biasing element receiving aperture being located through the heel panel.

In yet another aspect, the heel cup can further include a biasing element receiving aperture, the biasing element receiving aperture being located through the sole panel.

In yet another aspect, the heel cup can further include at least one biasing element attachment feature, the at least one biasing element attachment feature being provided in a form of a biasing element receiving aperture.

In yet another aspect, the heel cup can further include at least one biasing element receiving aperture.

In yet another aspect, the heel cup can further include at least one biasing element receiving aperture, the at least one biasing element receiving aperture being located in at least one of through the heel panel and through the sole panel.

In yet another aspect, the heel cup can further include at least one biasing element receiving aperture, the at least one biasing element receiving aperture being located in at least one of through the heel panel and through the sole panel.

In yet another aspect, the heel cup is fabricated of a formed silicone.

In yet another aspect, the heel cup is fabricated of a formed plastic.

In yet another aspect, the heel cup is fabricated of a formed nylon.

In yet another aspect, the heel cup is fabricated of a formed rubber.

In yet another aspect, the heel cup is fabricated of a formed polymer.

In yet another aspect, the heel cup is fabricated of a formed composite material.

In yet another aspect, the heel cup is fabricated of a formed fiber reinforced plastic.

In yet another aspect, the heel cup is fabricated of a formed glass reinforced plastic.

In yet another aspect, the heel cup is fabricated of a formed carbon fiber reinforced plastic.

In yet another aspect, the heel cup is fabricated of a formed composite material comprising a fiber material embedded in a resin, the resin being in a solid state.

In yet another aspect, the heel cup is fabricated of a formed composite material comprising a fiber material embedded in a resin, the fiber material being one of randomly arranged, flattened into a sheet (called a chopped strand mat), or woven into a fabric, the resin being in a solid state.

In yet another aspect, the heel cup is fabricated of a formed composite material comprising a fiber material being one of glass fibers, carbon fiber, and the like.

In yet another aspect, the heel cup is fabricated of one of: a formed silicone; a formed plastic; a formed nylon; a formed rubber; a formed polymer; a formed composite material; a formed fiber reinforced plastic; a formed glass reinforced plastic; a formed carbon fiber reinforced plastic; a formed composite material comprising a fiber material embedded in a resin, the resin being in a solid state; a formed composite material comprising a fiber material embedded in a resin, the fiber material being one of randomly arranged, flattened into a sheet (called a chopped strand mat), or woven into a fabric, the resin being in a solid state; a formed composite material comprising a fiber material being one of glass fibers, carbon fiber, and the like; or any other suitable material.

In yet another aspect, the heel cup is fabricated of at least one of: a formed silicone; a formed plastic; a formed nylon; a formed rubber; a formed polymer; a formed composite material; a formed fiber reinforced plastic; a formed glass reinforced plastic; a formed carbon fiber reinforced plastic; a formed composite material comprising a fiber material embedded in a resin, the resin being in a solid state; a formed composite material comprising a fiber material embedded in a resin, the fiber material being one of randomly arranged, flattened into a sheet (called a chopped strand mat), or woven into a fabric, the resin being in a solid state; a formed composite material comprising a fiber material being one of glass fibers, carbon fiber, and the like; or any other suitable material.

In yet another aspect, the heel cup is fabricated of at least two materials, the at least two materials selected from a group of materials comprising: silicone; plastic; nylon; rubber; polymer; composite material; fiber reinforced plastic; glass reinforced plastic; carbon fiber reinforced plastic; composite material comprising a fiber material embedded in a resin, the resin being in a solid state; composite material comprising a fiber material embedded in a resin, the fiber material being one of randomly arranged, flattened into a sheet (called a chopped strand mat), or woven into a fabric, the resin being in a solid state; composite material comprising a fiber material being one of glass fibers, carbon fiber, and the like; or any other suitable material.

In yet another aspect, the heel cup further comprising a biasing element seating recess.

In yet another aspect, the biasing element seating recess extending from the biasing element receiving aperture to the upper edge of the heel panel.

In yet another aspect, the biasing element seating recess extending from the biasing element receiving aperture located in the heel panel to the upper edge of the heel panel.

In yet another aspect, the biasing element seating recess extending from the biasing element receiving aperture located in the heel panel to the upper edge of the heel panel, the biasing element seating recess extending inward from an exterior surface of the heel cup.

In yet another aspect, the biasing element seating recess extending from the biasing element receiving aperture located in the heel panel to the upper edge of the heel panel, the biasing element seating recess extending inward from an interior surface of the heel cup.

In yet another aspect, the biasing element seating recess extending from the biasing element receiving aperture located in the sole panel to the upper edge of the heel panel.

In yet another aspect, the biasing element seating recess extending from the biasing element receiving aperture located in the sole panel, along the sole panel, along the heel panel, terminating the upper edge of the heel panel.

In yet another aspect, the elongated biasing element is fabricated of a material having elastic properties.

In yet another aspect, the elongated biasing element is fabricated of an elastic.

In yet another aspect, the elongated biasing element is fabricated of an elastomer.

In yet another aspect, the elongated biasing element is fabricated of a rubber.

In yet another aspect, the elongated biasing element is fabricated of one of: a natural rubber, a synthetic rubber, a nitrile rubber, a silicone rubber, a urethane rubber, a chloroprene rubber, an Ethylene Vinyl Acetate (EVA rubber).

In yet another aspect, the elongated biasing element is fabricated of a silicone.

In yet another aspect, the elongated biasing element is fabricated of an elastic polyurethane fiber or fabric.

In yet another aspect, the elongated biasing element is fabricated of a polyether-polyurea copolymer fabric, commonly referred to as spandex.

In yet another aspect, the elongated biasing element is fabricated of a neoprene rubber.

In yet another aspect, the elongated biasing element is fabricated of a foam neoprene rubber.

In yet another aspect, the elongated biasing element is fabricated of a stretch nylon.

In yet another aspect, the elongated biasing element further comprising an elongated biasing element retention formation.

In yet another aspect, the elongated biasing element further comprising a plurality of elongated biasing element retention formations spatially arranged from one end of the elongated biasing element.

In yet another aspect, the elongated biasing element further comprising a second plurality of elongated biasing element retention formations spatially arranged from a second end of the elongated biasing element, wherein the second end is longitudinally opposite of the first end.

In yet another aspect, the elongated biasing element further comprising an elongated biasing element retention formation, wherein a width of the elongated biasing element retention formation is greater than a width of the elongated biasing element.

In yet another aspect, the elongated biasing element further comprising an elongated biasing element retention formation, wherein a width of the elongated biasing element retention formation is greater than a width of the elongated biasing element and a dimension in an elongated direction of the biasing element receiving aperture of the heel cup.

In yet another aspect, the elongated biasing element further comprising an elongated biasing element retention formation, wherein a width of the elongated biasing element retention formation is greater than a width of the elongated biasing element and a dimension in an elongated direction of the biasing element receiving aperture of the waist band.

In yet another aspect, the elongated biasing element further comprising an elongated biasing element retention formation, wherein the elongated biasing element retention formation is provided at an end of the elongated biasing element.

In yet another aspect, the elongated biasing element further comprising a connector located at a first extended position of the elongated biasing element.

In yet another aspect, the elongated biasing element further comprising a connector located at a first extended position of the elongated biasing element and a mating connector assembled to the waist band.

In yet another aspect, the elongated biasing element further comprising a connector located at a first extended position of the elongated biasing element and a mating connector assembled to the heel cup.

In yet another aspect, the heel cup further comprising a bar extending through a center of the biasing element receiving aperture.

In yet another aspect, the heel cup further comprising a buckle formation located at the biasing element receiving aperture.

In yet another aspect, the heel cup further comprising a buckle formation located at the biasing element receiving aperture, the buckle formation comprising a buckle frame having an aperture and a bar extending through a center of the buckle frame aperture.

In yet another aspect, the waist band being fabricated of a flexible elastic material.

In yet another aspect, the waist band being fabricated of a flexible non-elastic material.

In yet another aspect, the waist band being fabricated of a woven fabric.

In yet another aspect, the waist band being fabricated of a non-woven material.

In yet another aspect, the waist band being fabricated of leather.

In yet another aspect, the waist band being fabricated of vinyl.

In yet another aspect, the waist band is fabricated of an elastomer.

In yet another aspect, the waist band is fabricated of a rubber.

In yet another aspect, the waist band is fabricated of one of: a natural rubber, a synthetic rubber, a nitrile rubber, a silicone rubber, a urethane rubber, a chloroprene rubber, an Ethylene Vinyl Acetate (EVA rubber).

In yet another aspect, the waist band is fabricated of a silicone.

In yet another aspect, the waist band is fabricated of an elastic polyurethane fiber or fabric.

In yet another aspect, the waist band is fabricated of a polyether-polyurea copolymer fabric, commonly referred to as spandex.

In yet another aspect, the waist band is fabricated of a neoprene rubber.

In yet another aspect, the waist band is fabricated of a foam neoprene rubber.

In yet another aspect, the waist band is fabricated of a stretch nylon.

In yet another aspect, the waist band includes a padded material.

In yet another aspect, the waist band includes a foam material.

In yet another aspect, the waist band further comprising a closure, wherein the closure adjustably joins a first longitudinal end of the waist band and a second, opposite longitudinal end of the waist band to one another.

In yet another aspect, the waist band further comprising a closure, the closure comprising a dense hook and loop tape combination.

In yet another aspect, the waist band further comprising a closure, the closure comprising a dense hook and loop tape combination, the dense hook being attached to a first surface of the waist band at a location proximate the first longitudinal end of the waist band and the dense loop being attached to a second, opposite surface of the waist band at a location proximate the second longitudinal end of the waist band.

In yet another aspect, the waist band further comprising a closure, the closure comprising a strap and buckle combination.

In yet another aspect, the waist band further comprising a closure, the closure comprising a strap and buckle combination, the strap being attached to the waist band at a location proximate the first longitudinal end of the waist band and the buckle being attached to the waist band at a location proximate the second longitudinal end of the waist band.

In accordance with a method of use, the hamstring support assembly worn and used in accordance with the following steps:
   securing a waist band of the hamstring support assembly to a waist of a patient, the hamstring support assembly comprising:
      the waist band,
      a heel cup comprising a sole panel and a heel panel, and
      an elongated biasing element extending between the waist band and the heel cup;
   positioning the heel cup to a heel of a leg of a patient, wherein the leg has or is recovering from a hamstring injury;
   adjusting a length of the elongated biasing element such that the elongated biasing element is in slight or neutral tension when the leg of the patient having the injured hamstring is fully extended; and
   moving the leg of the patient having the injured hamstring between a position where a knee of the leg of the patient having the injured hamstring is straight and a position where the knee of the leg of the patient having the injured hamstring is bent.

In yet another aspect, the step of adjusting the length of the elongated biasing element is accomplished by adjusting the elongated biasing element at a position proximate the waist band.

In yet another aspect, the step of adjusting the length of the elongated biasing element is accomplished by adjusting the elongated biasing element at a position proximate the heel cup.

In yet another aspect, the elongated biasing element assembly is provided as a plurality of elongated biasing element assemblies where at least one elongated biasing element of one elongated biasing element assembly and at least one second elongated biasing element of a second elongated biasing element assembly of the a plurality of elongated biasing element assemblies have different moduli of elasticity, the method further comprising steps of:
   selecting one elongated biasing element having a modulus of elasticity to provide a desired level of support to the diagnosed leg from the plurality of elongated biasing elements; and
   assembling the selected elongated biasing element having a modulus of elasticity to provide a desired level of support to the diagnosed leg between the waist band and the heel cup.

In yet another aspect, the heel cup further comprising a left side panel and a right side panel, wherein an interior surface of the left side panel and an interior surface of the right side panel are further included in defining the heel receiving cavity, the method further comprising a step of:
   retaining a lateral motion of the heel cup respective to the heel by seating the heel against the interior surface of the left side panel and the interior surface of the right side panel.

In yet another aspect, the elongated biasing element assembly being provided as a plurality of elongated biasing element assemblies where at least one elongated biasing element of one elongated biasing element assembly and at least one second elongated biasing element of a second elongated biasing element assembly of the a plurality of elongated biasing element assemblies have different moduli of elasticity, the method further comprising steps of:
   selecting one elongated biasing element having a modulus of elasticity to provide a desired level of support to the diagnosed leg from the plurality of elongated biasing elements; and
   assembling the selected elongated biasing element having a modulus of elasticity to provide a desired level of support to the diagnosed leg between the waist band and the heel cup.

In yet another aspect, the heel cup further comprising a left side panel and a right side panel, wherein an interior surface of the left side panel and an interior surface of the right side panel are further included in defining the heel receiving cavity, the method further comprising a step of:
   retaining a lateral motion of the heel cup respective to the heel by seating the heel against the interior surface of the left side panel and the interior surface of the right side panel.

In yet another aspect, the method further comprising a step of:
   placing a shoe onto the foot of the diagnosed leg, wherein the shoe sandwiches the sole panel and at least a portion of the rear panel between the shoe and the foot of the diagnosed leg.

In yet another aspect, the elongated biasing element assembly further comprising an elongated biasing element, the heel cup further comprising a biasing element seating recess, the method further comprising a step of positioning the elongated biasing element within the biasing element seating recess.

In yet another aspect, the elongated biasing element assembly further comprising an elongated biasing element, the method further comprising a step of positioning the waist band about the waist of the patient such to arrange the elongated biasing element to be substantially parallel to the diagnosed leg.

In yet another aspect, the method further comprising a step of placing a pliant material between a body of the heel cup and the heel.

In yet another aspect, the heel cup further comprising at least one of: a rear panel biasing element receiving aperture formed through the rear panel and a sole panel biasing element receiving aperture formed through the sole panel, the method further comprising a step of assembling the elongated biasing element assembly to one of the rear panel biasing element receiving aperture and the sole panel biasing element receiving aperture.

In yet another aspect, the elongated biasing element assembly further comprising one of a male connector or a female connector, and a mating connector of the one of the male connector and a female connector connected to one of the waist band or the heel cup, the method further comprising a step of connecting the one of the male connector or the female connector to the mating connector of the one of the male connector and a female connector.

In yet another aspect, the heel cup is fabricated of a material that transitions from a rigid state to a moldable state when elevated in temperature to a temperature that is above ambient temperature, the method further comprising steps of:
  elevating a temperature of the heel cup to a temperature above ambient, where the material of the heel cup becomes moldable; and
  molding the heel cup against the heel of the injured leg of the patient.

In yet another aspect, the method further comprising steps of:
  securing a waist band to a waist of a patient, the patient comprising a diagnosed leg, wherein the diagnosed leg is diagnosed as one of: (a) having a hamstring injury or (b) recovering from the hamstring injury;
  securing an elongated biasing element to a heel cup, the heel cup comprising a sole panel and a heel panel, wherein an interior surface of the sole panel and an interior surface of the heel panel define a heel receiving cavity; and
  securing the elongated biasing element to the waist band.

In yet another aspect, the method further comprising a step of seating the heel cup to a heel of a patient by placing the heel within the heel receiving cavity, wherein the heel is a portion of a foot of the diagnosed leg.

In yet another aspect, the method further comprising a step of seating the heel cup to a heel of a patient by placing the heel within the heel receiving cavity, wherein the heel is a portion of a foot of the diagnosed leg.

These and other aspects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, in which.

Like reference numerals refer to like parts throughout the several views of the drawings.

DETAILED DESCRIPTION

Detailed embodiments of the present invention are disclosed herein. It will be understood that the disclosed embodiments are merely exemplary of the invention that may be embodied in various and alternative forms. The figures are not necessarily to scale, and some features may be exaggerated or minimized to show details of particular embodiments, features, or elements. Specific structural and functional details, dimensions, or shapes disclosed herein are not limiting but serve as a basis for the claims and for teaching a person of ordinary skill in the art the described and claimed features of embodiments of the present invention. The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
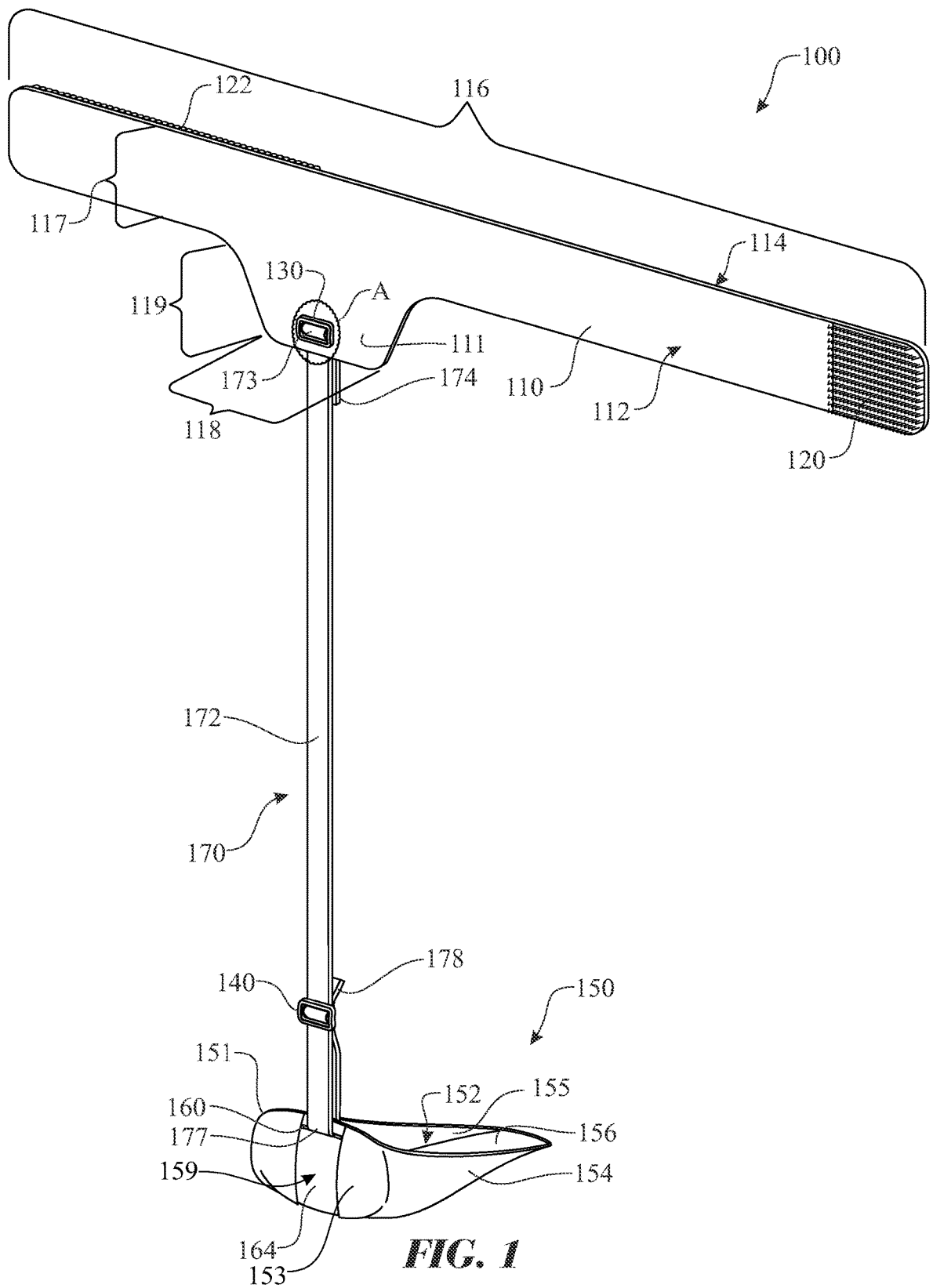
FIG. 1 presents an isometric rear view of an exemplary hamstring support assembly, the lanyard system comprising an exemplary waist band, an exemplary heel cup, and an exemplary elongated biasing element extending between the waist band and the heel cup.
Figure 2:
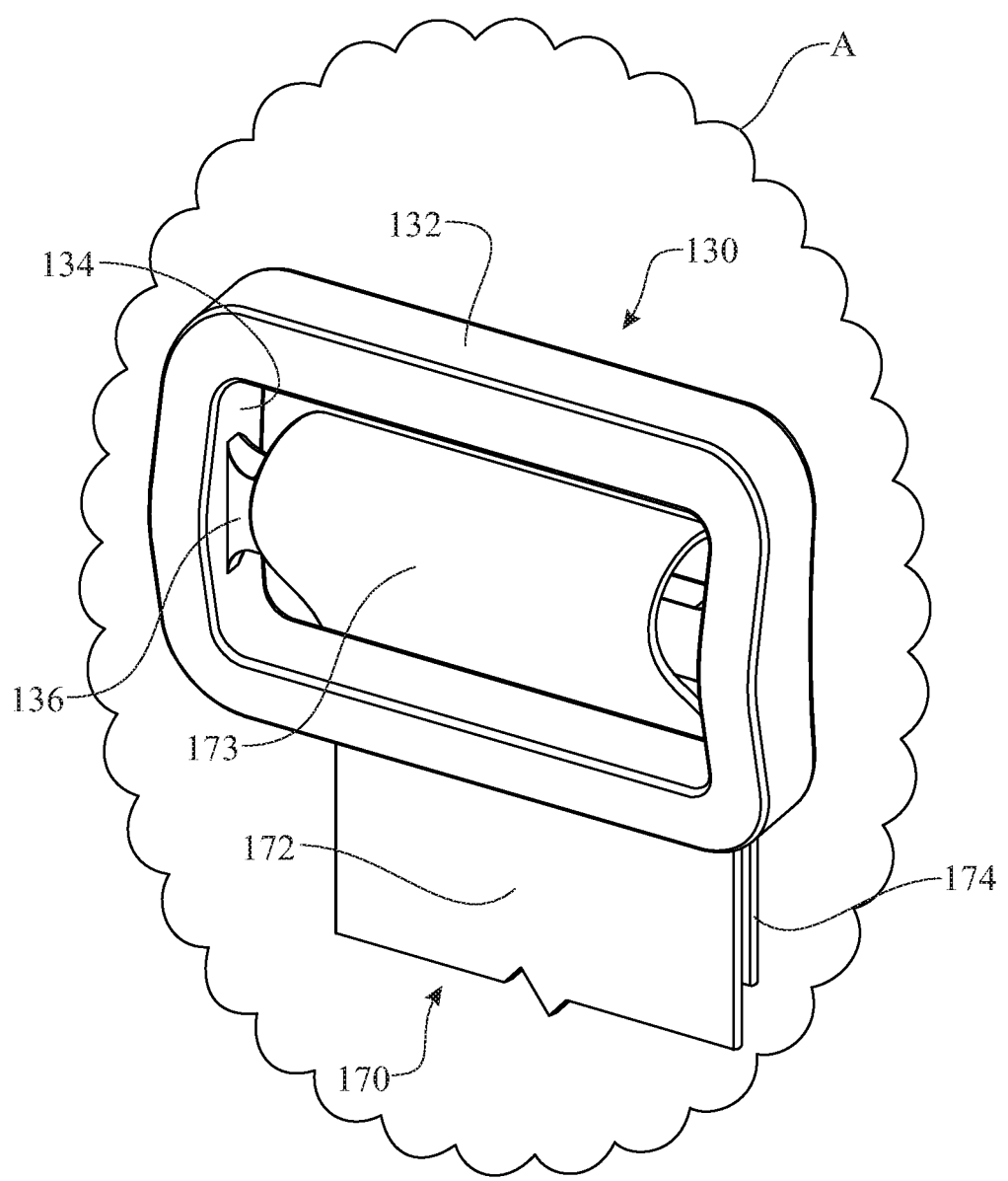
FIG. 2 presents an isometric elevation view of an exemplary biasing element retention buckle associated with the exemplary hamstring support assembly originally introduced in FIG. 1.
Figure 7:
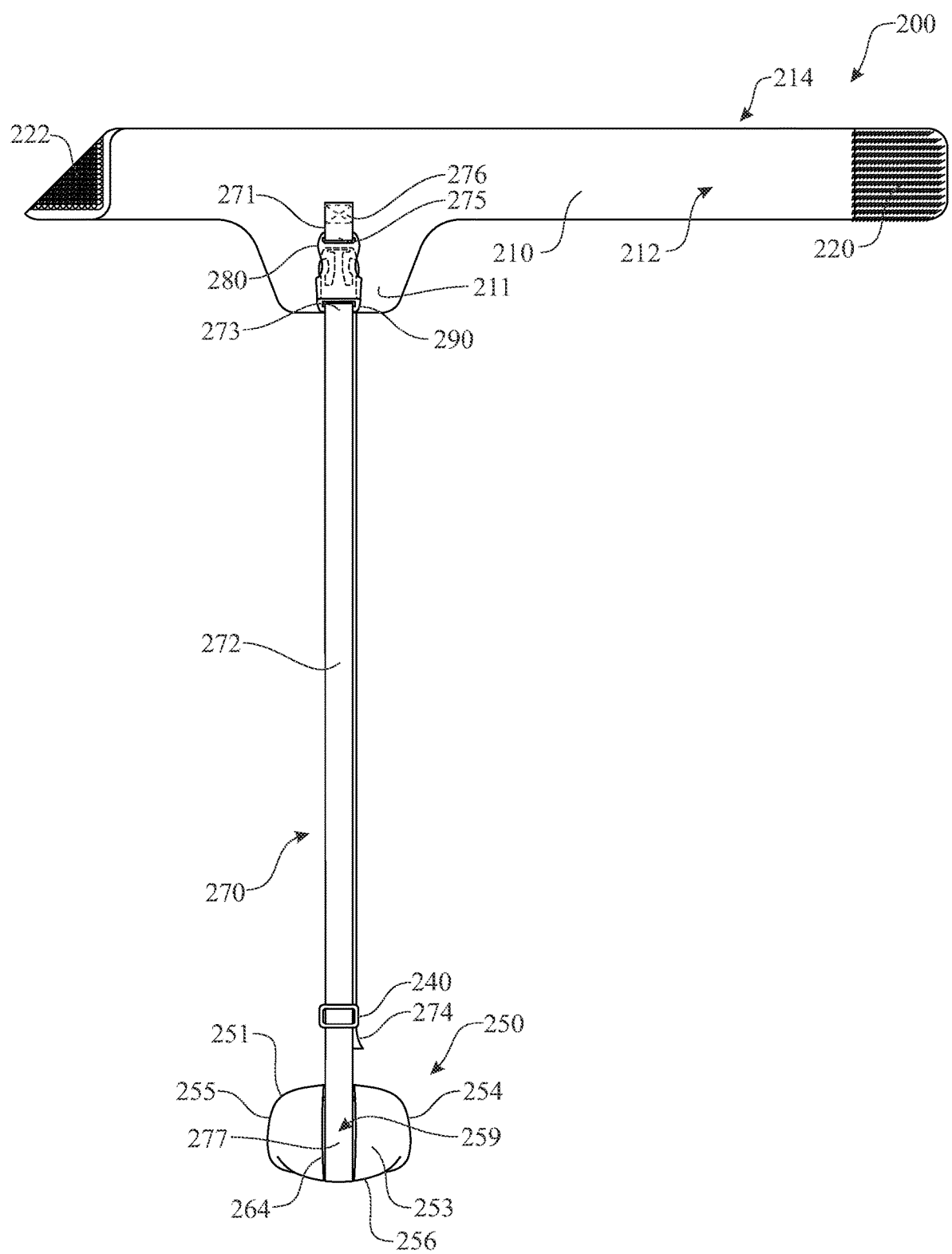
FIG. 7 presents a rear view of an exemplary modified hamstring support assembly, the exemplary modified hamstring support assembly comprising an exemplary waist band, an exemplary heel cup, and an exemplary modified elongated biasing element extending between the waist band and the heel cup.
Figure 8:
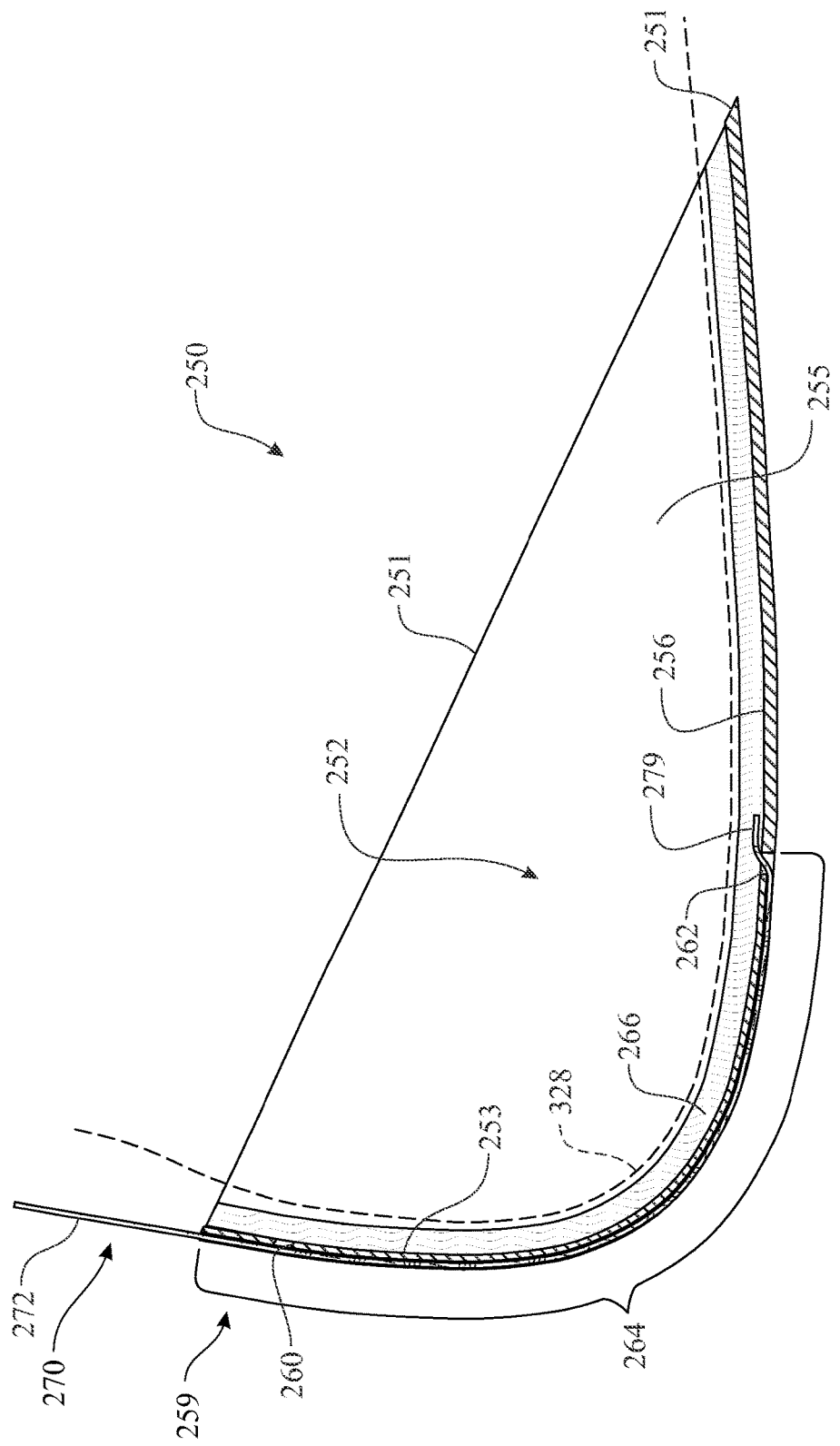
FIG. 8 presents a sectioned side view of the exemplary heel cup of the exemplary hamstring support assembly originally introduced in FIG. 7, the section taken along section line 6-6 of FIG. 4, a longitudinal centerline of the heel cup, the illustration presenting a second arrangement for attachment of the elongated biasing element to the heel cup.
Figure 9:
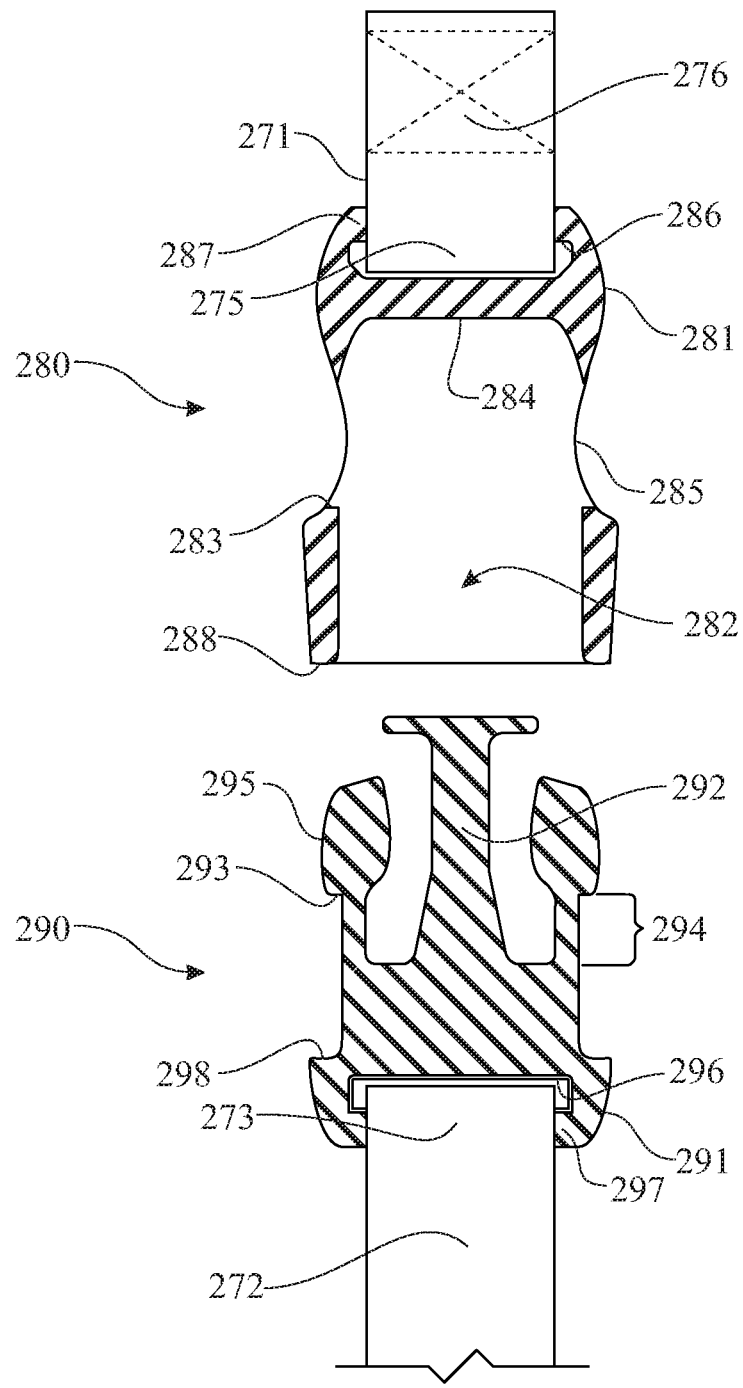
FIG. 9 presents a section view of an exemplary elongated biasing element connector arrangement for connection of the elongated biasing element to the waist band, wherein the exemplary connector arrangement is originally introduced in FIG. 7.
Figure 10:
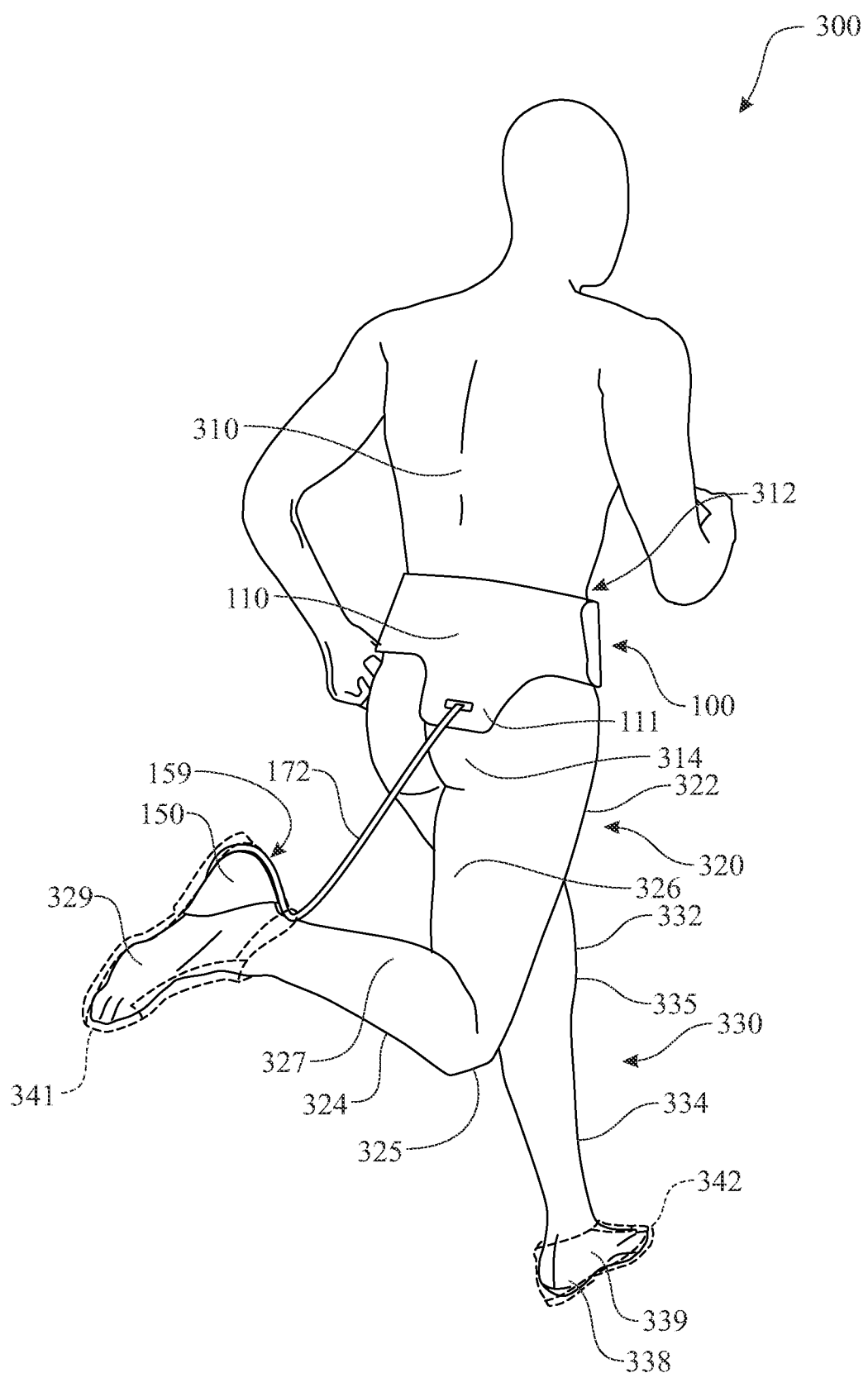
FIG. 10 presents a perspective view of a patient wearing and using the exemplary modified hamstring support assembly originally introduced in FIG. 1, the illustration presenting the patient positioning a leg having the injured hamstring in a bent position.
Figure 11:
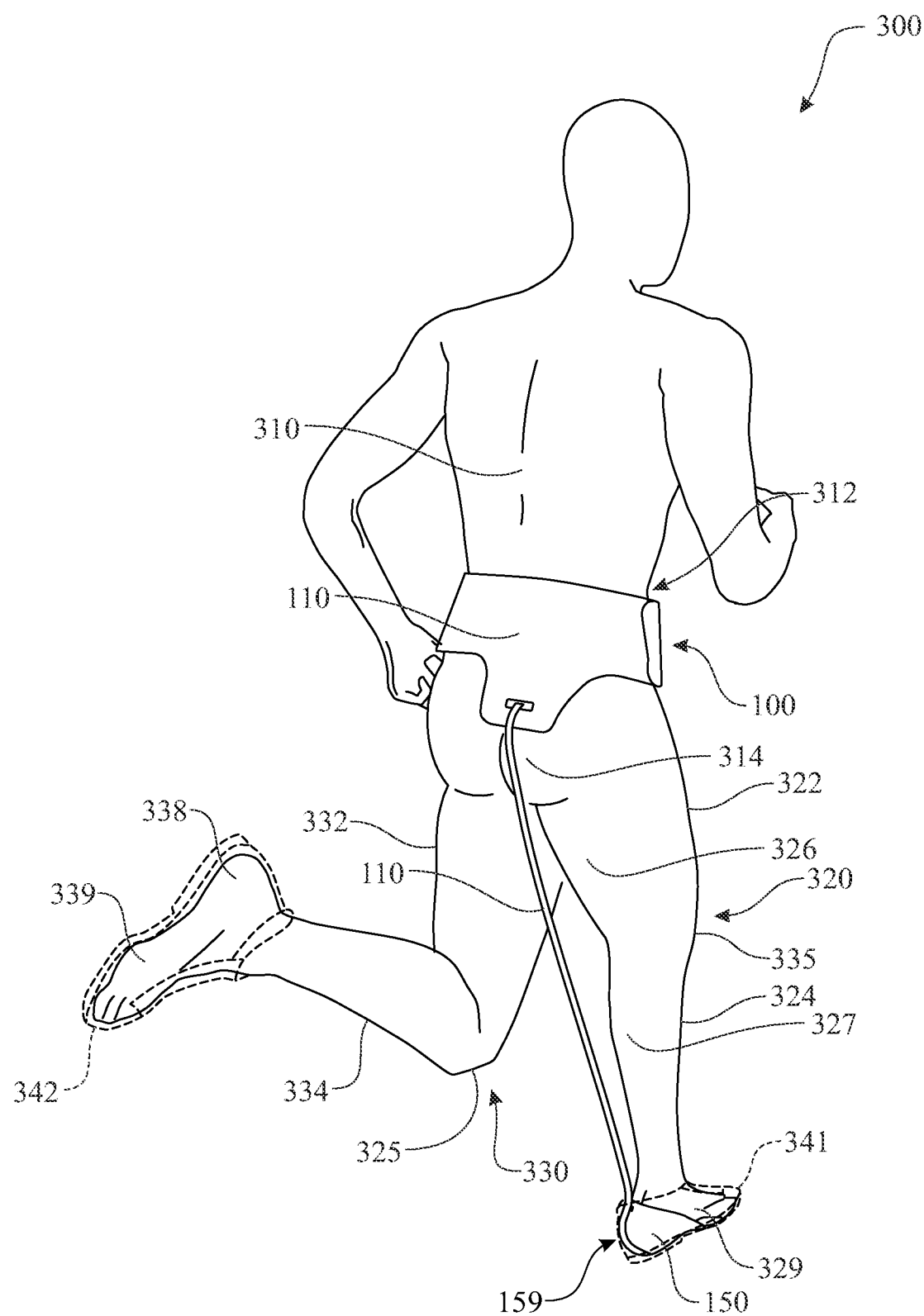
FIG. 11 presents a perspective view of a patient wearing and using the exemplary modified hamstring support assembly originally introduced in FIG. 1, the illustration presenting the patient positioning a leg having the injured hamstring in an extended position.

A hamstring support assembly 100 provides support to a patient addressing an injured hamstring, the hamstring support assembly 100 being introduced in an illustration shown in FIG. 1, with details being presented in illustrations presented in FIGS. 2 through 6. A hamstring support assembly 200 is a hamstring support assembly 100 including a modified version of the elongated biasing element assembly, as illustrated in FIGS. 7, 8, and 9. The hamstring support assembly 100 and hamstring support assembly 200 are used to aid in recovery of a patient having an injured hamstring. The illustrations presented in FIGS. 10 and 11 illustrate a patient 300 wearing the hamstring support assembly 100, where FIG. 10 presents the patient 300 having the injured leg 320 shown bent at a knee 325 and where FIG. 11 presents the patient 300 having the injured leg 320 shown extended at the knee 325

The hamstring support assembly 100 can include a waist strap 110, a heel cup 150 and an elongated biasing element assembly 170 elastically connecting the waist strap 110 and the heel cup 150 with one another.

Figure 3:
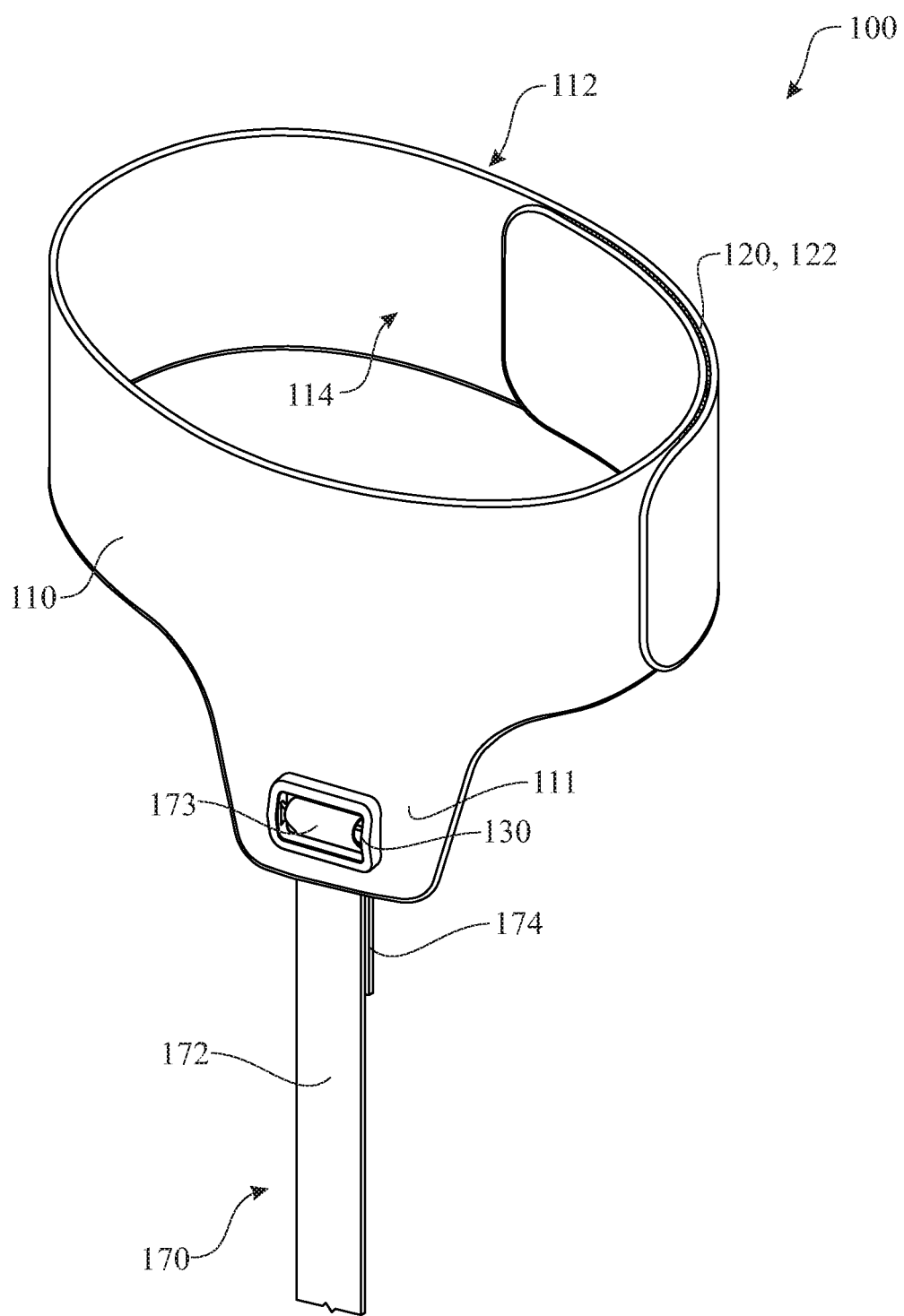
FIG. 3 presents an isometric top view of a waistband portion of the exemplary hamstring support assembly originally introduced in FIG. 1.

The waist strap 110 can be shaped having an elongated portion having a waist strap elongated length 116 and a waist strap traversing height 117 and a waist strap tail section 111 extending downward from the waist strap 110. The waist strap tail section 111 is illustrated having a waist strap support attachment tab horizontal dimension 118 and a waist strap attachment tab vertical height 119. The waist strap tail section 111 provides a section of material for supporting of the waist band biasing element retention buckle 130 or similar strap receiving element. The waist strap 110 includes at least one feature for joining a first end of the waist strap 110 and a second, opposite end of the waist strap 110 to one another. The at least one feature for joining the first end of the waist strap 110 and the second, opposite end of the waist strap 110 to one another can be any suitable feature or pair of components, preferably enabling sizing of a circumference of the waist strap 110 when placed in a loop, as shown in FIG. 3. The exemplary illustration shows a waist strap 110 employing a first dense hook and loop tape segment 120 attached to a waist strap first outer surface 112 of the waist strap 110 at a first elongated end of the waist strap 110 and a second, mating dense hook and loop tape segment 122 attached to a waist strap second outer surface 114 of the waist strap 110 at a second, opposite elongated end of the waist strap 110. The first dense hook and loop tape segment 120 and the second, mating dense hook and loop tape segment 122 are engaged with one another joining the first elongated end of the waist strap 110 and the second, opposite elongated end of the waist strap 110 to retain the waist strap 110 at a desired circumferential size about a waistline 312 of the recovering patient 300, as shown in FIGS. 3, 10, and 11. The pair of components provided for joining the first elongated end of the waist strap 110 and the second, opposite elongated end of the waist strap 110 can be of any suitable connecting interface enabling adjustability. It is preferred that the connecting interface would enable unlimited or infinite adjustability, such as the ability provided by the first dense hook and loop tape segment 120 and the second, mating dense hook and loop tape segment 122. Alternative connecting interfaces can include a buckle and an insertable strap section, a hook and a series of eyelets or loops, an eyelet or loop and a series of hooks, a snap socket and a series of snap studs, a snap stud and a series of snap sockets, a tie element and a mating anchor, a first tie element and a second tie element, or any other suitable connecting interface.

The waist strap 110 is fabricated of a flexible sheet of material. In one consideration, the material of the waist strap 110 have elastic properties. In a second consideration, the material of the waist strap 110 can be non-elastic. The waist strap 110 can be fabricated of a flexible material, a flexible elastic material, a flexible non-elastic material, a woven fabric, a non-woven material, leather, vinyl, an elastomer, a rubber, a natural rubber, a synthetic rubber, a nitrile rubber, a silicone rubber, a urethane rubber, a chloroprene rubber, a neoprene rubber, a foam neoprene rubber, an Ethylene Vinyl Acetate (EVA rubber), a silicone, an elastic polyurethane fiber or fabric, a polyether-polyurea copolymer fabric (commonly referred to as spandex), and a stretch nylon. The waist strap 110 can be fabricated of a layered arrangement of materials. For example, the waist strap 110 can be fabricated of fabric covered neoprene rubber.

The waist strap 110 can additionally include a padded material, a foam material, and any other flexible material that would provide additional comfort to the patient while being worn, while providing adequate support during use.

Figure 4:
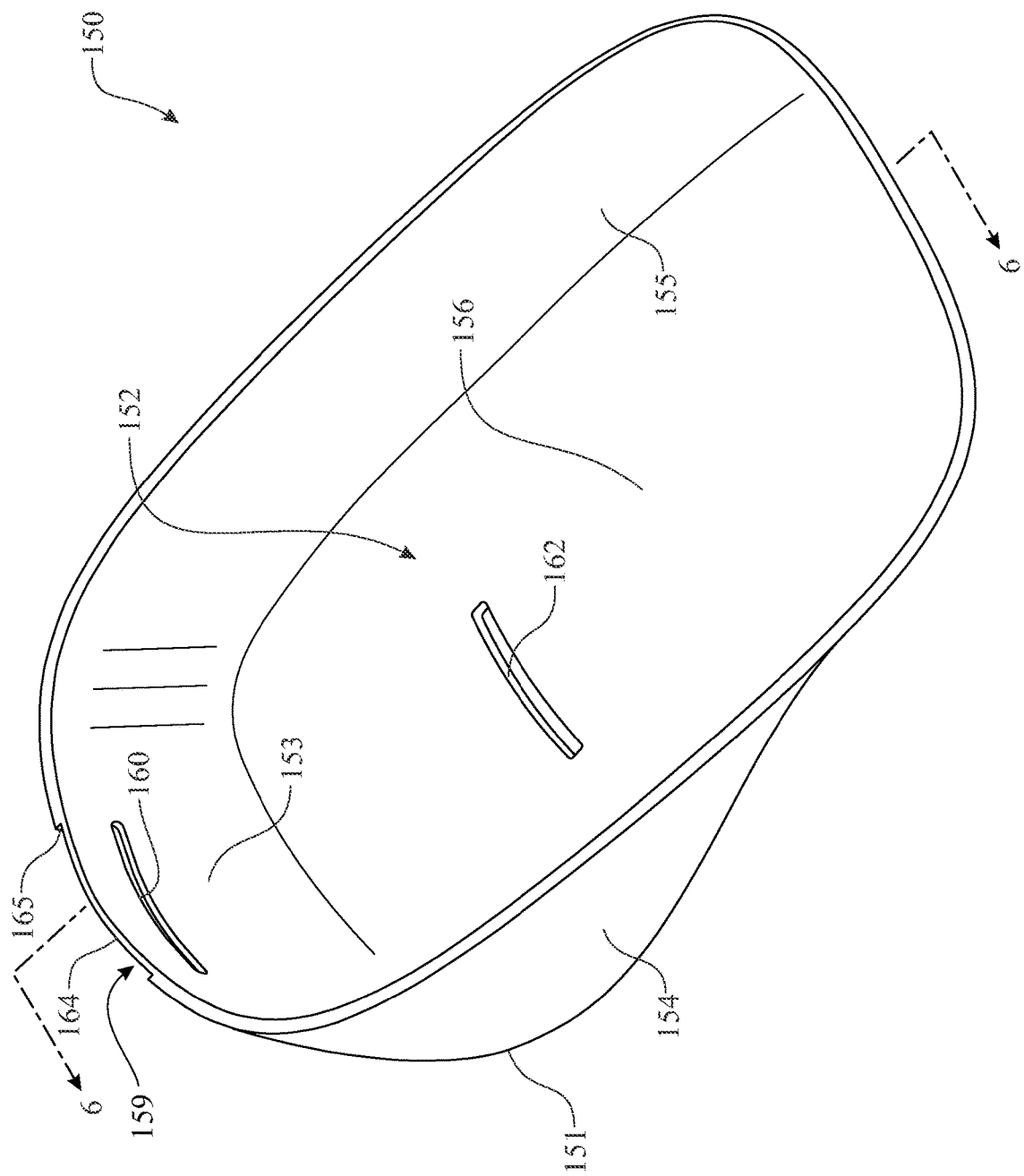
FIG. 4 presents an isometric top view of the exemplary heel cup of the exemplary hamstring support assembly originally introduced in FIG. 1.
Figure 5:
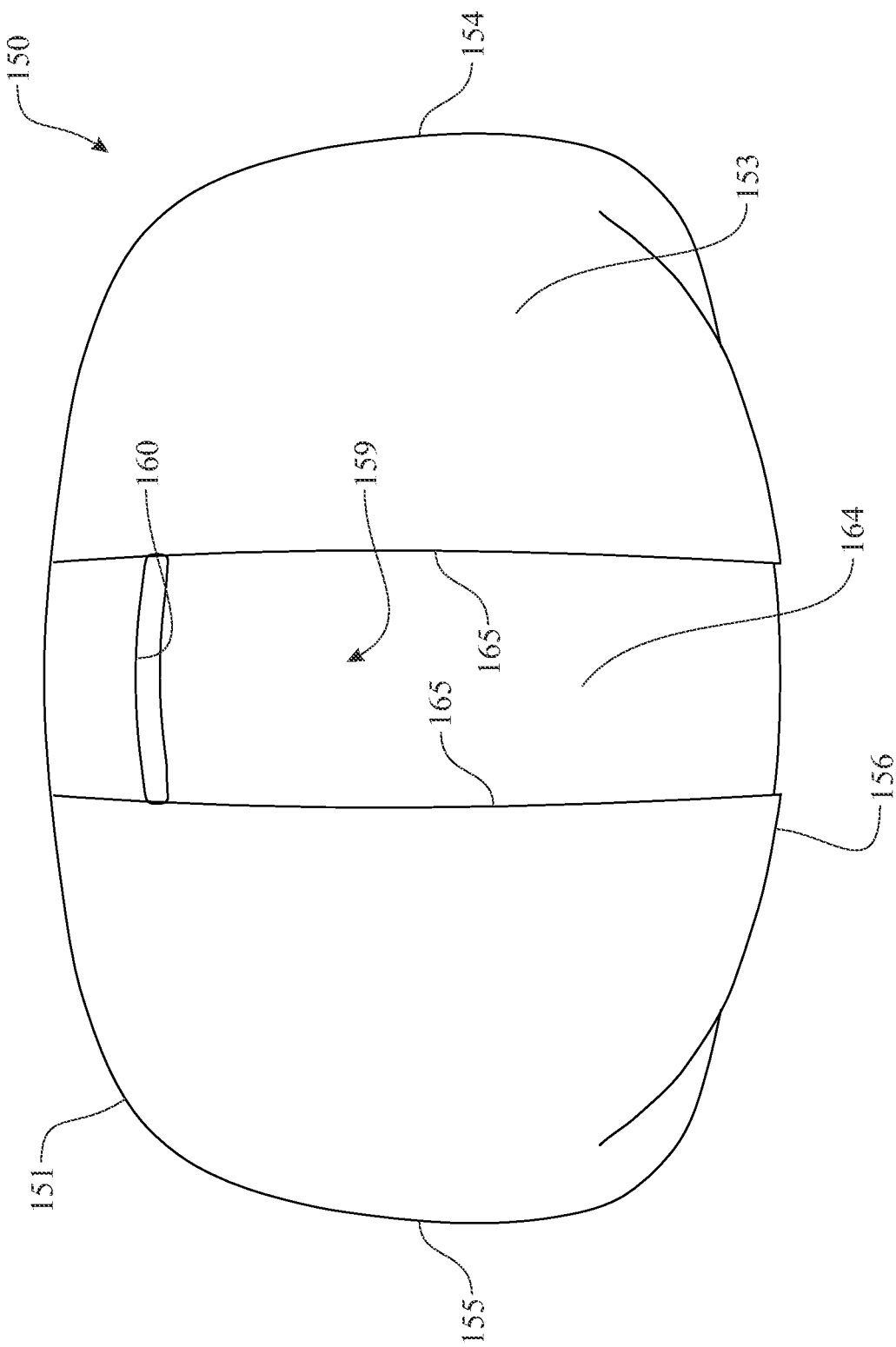
FIG. 5 presents a rear elevation view of the exemplary heel cup of the exemplary hamstring support assembly originally introduced in FIG. 1.
Figure 6:
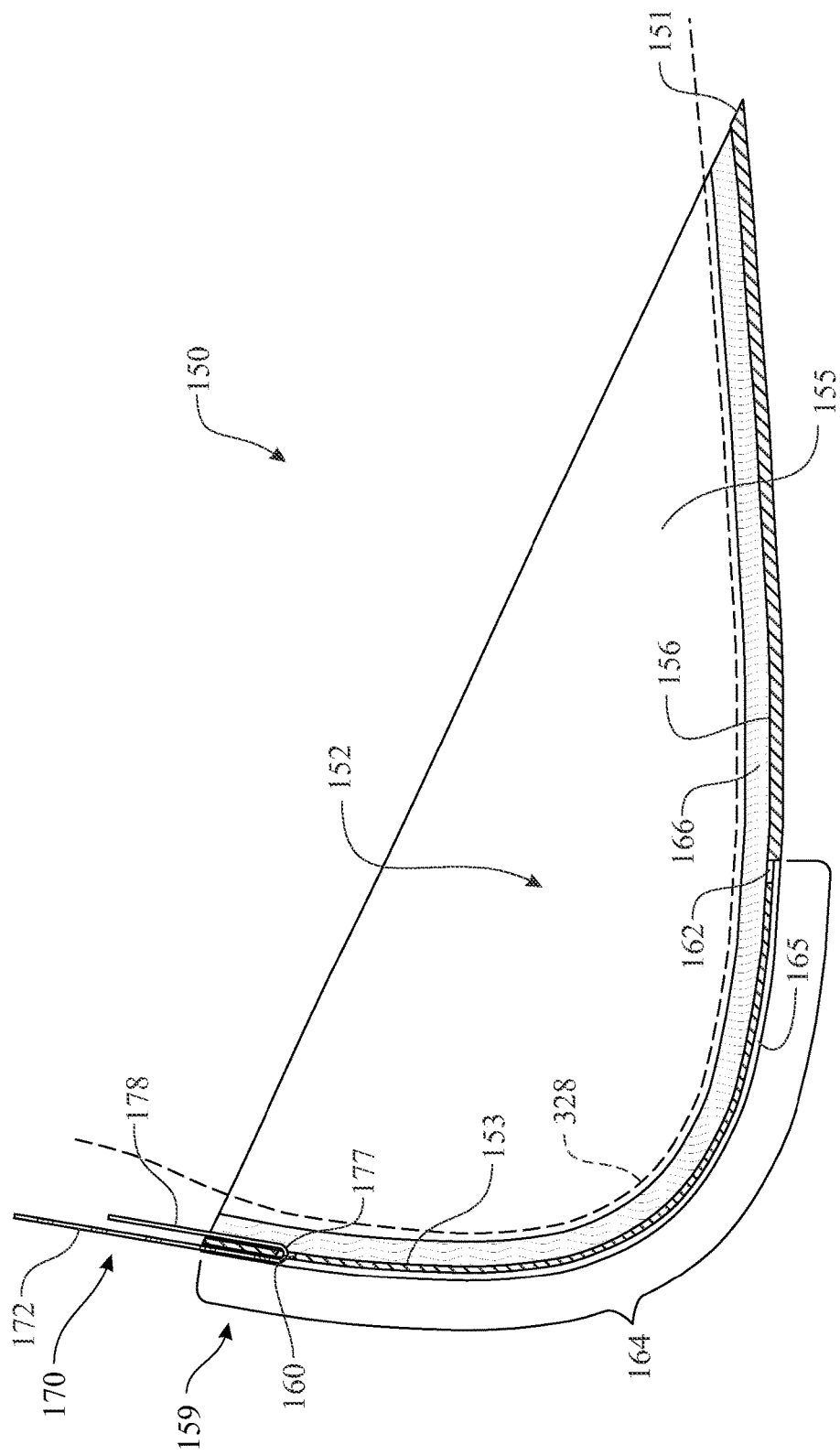
FIG. 6 presents a sectioned side view of the exemplary heel cup of the exemplary hamstring support assembly originally introduced in FIG. 1, the section taken along section line 6-6 of FIG. 4, a longitudinal centerline of the heel cup, the illustration presenting a first arrangement for attachment of the elongated biasing element to the heel cup.

The heel cup 150 is detailed in the illustrations presented in FIGS. 4 through 6. The heel cup comprises a heel cup body 151 defining a heel receiving cavity 152 which has a shape that contours a heel of an injured leg 320 of a recovering patient 300. The heel cup body 151 can be considered the primary formation of the heel cup 150. Other materials can be assembled to the heel cup body 151, such as a pliant material 166 for comfort. The pliant material 166 is preferably located at points of contact and inflection when the heel cup 150 is placed upon the heel. The heel cup body 151 includes a heel cup heel (rear) panel 153 and a heel cup soul panel 156. The heel cup body 151 is preferably fabricated with the heel cup heel (rear) panel 153 and the heel cup soul panel 156 being continuous with one another. The heel cup body 151 is preferably fabricated with the heel cup heel (rear) panel 153 and the heel cup soul panel 156 being continuous with one another, wherein a transition between the heel cup heel (rear) panel 153 and the heel cup soul panel 156 is smooth and comprises an arched transition, as best shown in FIG. 6. A width of the heel cup soul panel 156 is preferably a width proximate a like width of an injured leg foot 329 of the recovering patient 300 (FIGS. 10 and 11). The heel cup body 151 can be reinforced by introducing a heel cup right side panel 154 and a heel cup left side panel 155. Each of the heel cup right side panel 154 and the heel cup left side panel 155 extend generally vertically from a respective edge of the heel cup soul panel 156. A transition between the heel cup soul panel 156 and the respective side panel 154, 155 is preferably arched, as best shown in FIG. 5. Similarly, a transition between the heel cup heel (rear) panel 153 and the respective side panel 154, 155 is preferably arched, as best shown in FIG. 4.

The heel cup side panels 154, 155 can have an upper edge an upper edge extending between a respective upper edge of the heel panel 153 and a respective forward edge of the sole panel 156. The upper edge of each heel cup side panel 154, 155 can be linear, arched, or of any other suitable shape. The upper edge of each heel cup side panel 154, 155 can be shaped to include a generally vertical segment extending upward from the respective forward edge of the sole panel 156, transitioning to a direction towards the upper edge of the heel panel 153. The heel receiving cavity 152 is defined by interior surfaces of the heel cup heel (rear) panel 153, the heal cup right side panel 154, the heal cup left side panel 155, and the heel cup soul panel 156.

The heel cup 150 can include one or more features for assembly and management of the elongated biasing element 172. A heel panel biasing element receiving aperture 160 can be provided through the heel cup heel (rear) panel 153. A sole panel biasing element receiving aperture 162 can be provided through the heel cup soul panel 156. The heel cup 150 can include one or both of the heel panel biasing element receiving aperture 160 and the sole panel biasing element receiving aperture 162. A biasing element seating recess 164 can be formed extending inward from an exterior surface of the heel cup heel (rear) panel 153, as illustrated in FIGS. 4 through 6. The biasing element seating recess 164 is defined by a biasing element seating recess sidewall 165 formed along each edge thereof. In an alternative design, the biasing element seating recess can be formed extending inward from an interior surface of the heel cup heel (rear) panel 153. In one arrangement, the biasing element seating recess 164 can extend from the heel panel biasing element receiving aperture 160 to an upper edge of the heel cup heel (rear) panel 153. In a second arrangement, the biasing element seating recess 164 can extend from the sole panel biasing element receiving aperture 162 to an upper edge of the heel cup heel (rear) panel 153. The biasing element seating recess 164 would preferably have a depth that is substantially equal or slightly greater than a thickness of the elongated biasing element 172. By recessing the elongated biasing element 172, the design accommodates the thickness of the elongated biasing element 172 where the thickness of the elongated biasing element 172 would not impact or aggravate the recovering patient 300 during use. Additionally, the biasing element seating recess sidewalls 165 defining the biasing element seating recess 164 retain the elongated biasing element 172 from unwanted lateral movement.

The heel cup 150 can be fabricated of any suitable material. It is preferred that the material be at least slightly pliant, providing comfort to the recovering patient 300. The heel cup 150 can be fabricated of a material selected from a group of suitable heel cup materials. The group of suitable heel cup materials includes: silicone; plastic; nylon; rubber; polymer; composite material; fiber reinforced plastic; glass reinforced plastic; carbon fiber reinforced plastic; a fiber material embedded in a resin; the resin being in a solid state; a formed composite material comprising; a formed composite material comprising a fiber material embedded in a resin; the fiber material being one of randomly arranged; flattened into a sheet (called a chopped strand mat); or woven into a fabric; the resin being in a solid state; a formed composite material comprising a fiber material being one of glass fibers, carbon fiber, and the like; or any other suitable material.

In one manufacturing process, each heel cup 150 would be formed using standard sized forms. The heel cup body 151 can be fabricated of a pliant material enabling formation to the respective heel 328 of the injured leg 320. The heel cup body 151 can be fabricated of a formable material, wherein the recovering patient 300 would heat the heel cup body 151 to a predetermined temperature (based upon the selected material) and placed against the respective heel 328 of the injured leg 320. The heel cup body 151 can be compressed against the respective heel shaping the heel cup body 151 to contour to the patient's heel. The process can be enhanced by placing the heel of the patient, including the heel cup 150, into a bag and a vacuum can be drawn on the bag to aid in forming the heel cup body 151 to the respective heel.

The heel cup body 151 can be fabricated of at least one material selected from the group of suitable heel cup materials. In another arrangement, the heel cup body 151 is fabricated of at least two materials, the at least two materials selected from the group of heel cup suitable materials. The materials can be provided in any arrangement. In one suggested arrangement, a first material can be laminated upon a surface of a second material. For example, a pliant material 166 can be laminated onto an interior surface of a more rigid material of the heel cup body 151, wherein the more rigid material used for the heel cup body 151 is provided to support the elongated biasing element assembly 170 and the pliant material 166 is provided for comfort to the recovering patient 300.

An upper end of the elongated biasing element assembly 170 is assembled to the waist strap 110 and a lower end of the elongated biasing element assembly 170 is assembled to the heel cup 150. The assembly of the elongated biasing element assembly 170 to the waist strap 110 is as follows:

The elongated biasing element assembly 170 can be secured to the waist strap 110 using any suitable attachment interface. The exemplary attachment interface utilizes a waist band biasing element retention buckle 130, which is detailed in section A, enlarged in FIG. 2. The waist band biasing element retention buckle 130 includes a waist band biasing element retention buckle frame 132 that can be of any suitable shape and size. A waist band biasing element retention buckle aperture surface 134 of the waist band biasing element retention buckle frame 132 defines a passageway for receiving an elongated biasing element waist securing formation 173 of an elongated biasing element 172. The elongated biasing element waist securing formation 173 is routed over or around a waist band biasing element retention buckle bar 136 of the waist band biasing element retention buckle 130. The waist band biasing element retention buckle bar 136 is arranged spanning across an elongated direction of the passageway. The elongated biasing element 172, elongated biasing element waist securing formation 173, and elongated biasing element waist securing formation tail 174 can be routed along any suitable path to secure the elongated biasing element 172 sizing the elongated biasing element 172 to a desired length. It is understood that the waist band biasing element retention buckle 130 can include any configuration to enable adjustability of the length of the elongated biasing element 172. The preferred configurations would enable infinite number of adjusted lengths of the elongated biasing element 172. In a less preferred configuration, the waist band biasing element retention buckle 130 can include a prong, which would be inserted through one or more holes formed through the elongated biasing element waist securing formation 173. In the exemplary illustration, the waist band biasing element retention buckle 130 is assembled to a tail section 111 of the waist strap 110. In one configuration, the waist band biasing element retention buckle 130 can be integral with the waist strap 110. In an alternative arrangement, the waist band biasing element retention buckle 130 can be replaced by an aperture, a frame having an aperture (the waist band biasing element retention buckle 130 exclusive of the waist band biasing element retention buckle bar 136), and the like.

The assembly of the elongated biasing element assembly 170 to the heel cup 150 is as follows:

The elongated biasing element assembly 170 can be secured to a heel posterior end 159 of the heel cup 150 using any suitable attachment interface. The exemplary attachment, as illustrated in FIGS. 1 and 6 routes the elongated biasing element 172 through a heel cup biasing element retention buckle 140, continuing through the heel panel biasing element receiving aperture 160, looping around a portion of the heel cup heel (rear) panel 153 above the heel panel biasing element receiving aperture 160, creating an elongated biasing element heel cup securing formation 177, and returning to the heel cup biasing element retention buckle 140. Once joined, an elongated biasing element heel cup securing formation tail 178 remains free from an opposite side of the heel cup biasing element retention buckle 140. The heel cup biasing element retention buckle 140 retains registration of the elongated biasing element heel cup securing formation tail 178 and the elongated biasing element assembly 170 respective to one another, thus retaining a set distance of the elongated biasing element assembly 170 between the waist strap 110 and the heel cup 150.

The above described assembly of the elongated biasing element assembly 170 to the waist strap 110 and the heel cup 150 is only one exemplary method of joining the elongated biasing element assembly 170 to the waist strap 110 and the heel cup 150. A second exemplary method of joining the elongated biasing element assembly to the waist band and the heel cup is provided in FIGS. 7, 8, and 9. The hamstring support assembly 100 and the hamstring support assembly 200 include a number of like elements. Like elements of the hamstring support assembly 200 and the hamstring support assembly 100 are numbered the same, with the elements associated with the hamstring support assembly 200 being preceded by the numeral "2". Distinctions between the hamstring support assembly 100 and the hamstring support assembly 200 are described herein.

The elongated biasing element assembly 170 is configured to be secured directly to the waist band biasing element retention buckle 130 integrated into the waist strap 110. In the hamstring support assembly 200, an elongated biasing element assembly 270 is secured to a waist strap 210 by a pair of mating connector components; more specifically, a biasing element female connector 280 and a biasing element male connector 290. The biasing element female connector 280 is carried by the waist strap 210. In the exemplary illustration, the biasing element female connector 280 is assembled to the waist strap 210 by a biasing element connector strap 271. A first end of the biasing element connector strap 271 forms a biasing element connector, connector attachment strap portion 275, which loops around a biasing element female connector strap attachment bar 287 of the biasing element female connector 280, as illustrated in FIG. 9. The second opposite end is assembled to the waist strap 210 by any suitable attachment scheme. In the exemplary illustration a biasing element connector waist band attachment strap portion 276 is secured to the waist strap 210. The biasing element connector waist band attachment strap portion 276 can be secured to the waist strap 210 using stitching, an adhesive, or any other suitable connection interface. Although the exemplary illustration provides a preferred method for assembling the biasing element female connector 280 to the waist strap 210, it is understood that any suitable scheme for assembling the biasing element female connector 280 to the waist strap 210 can be employed. The elongated biasing element 272 is assembled to the biasing element male connector 290 by routing the elongated biasing element 272 through the biasing element male connector strap passage aperture 296 of the biasing element male connector 290, as illustrated in FIG. 9. The elongated biasing element 272 forms an elongated biasing element waist band buckle securing formation 273 as the elongated biasing element 272 loops over a biasing element male connector strap attachment bar 297 of the biasing element male connector 290. A biasing element length adjusting buckle 240 is carried by the elongated biasing element 272 at a location to engage with a second, continuing segment of the elongated biasing element 272. The second, continuing or returning segment of the elongated biasing element 272 is also threaded through the biasing element length adjusting buckle 240, where the biasing element length adjusting buckle 240 retains a relationship between the front segment of the elongated biasing element 272 and the second, continuing segment of the elongated biasing element 272, thus maintaining a length between the biasing element male connector 290 and the biasing element length adjusting buckle 240. An elongated biasing element length adjusting buckle securing formation tail 274 extends from the second, continuing segment of the elongated biasing element 272, as the second, continuing segment of the elongated biasing element 272 passes through the biasing element length adjusting buckle 240. The retention function of the biasing element length adjusting buckle 240 establishes and upholds a distance between the waist strap 210 and the heel cup 250. The elongated biasing element heel cup securing formation 277 of the elongated biasing element assembly 270 is routed being seated within the biasing element seating recess 264 and secured to a heel posterior end 259 of the heel cup 250 by inserting an elongated biasing element retention formation 279 through a sole panel biasing element receiving aperture 262 and seating an edge of the elongated biasing element assembly 270 against an area of a heel cup soul panel 256 surrounding the sole panel biasing element receiving aperture 262. The routing of the elongated biasing element heel cup securing formation 277 is best illustrated in FIG. 8. The elongated biasing element retention formation 279 is of a shape and size where a lateral dimension of the elongated biasing element retention formation 279 is greater than an elongated dimension of the heel panel biasing element receiving aperture 260. The elongated biasing element retention formation 279 would be compressed during insertion through the heel panel biasing element receiving aperture 260 and returns to a normal state following the insertion process. The injured leg foot 329 of the recovering patient 300 would prevent the elongated biasing element retention formation 279 from slipping through the heel panel biasing element receiving aperture 260 during use. When included, a pliant material 266 placed upon the interior surface of the heel cup body 251 would prevent the elongated biasing element retention formation 279 from slipping through the heel panel biasing element receiving aperture 260 during use. The biasing element seating recess sidewall (reference to the biasing element seating recess sidewall 165) prevents the elongated biasing element heel cup securing formation 277 from any lateral movements, thus retaining the elongated biasing element heel cup securing formation 277 within the biasing element seating recess 264 during use.

Details of the biasing element female connector 280 and the biasing element male connector 290 are presented in FIG. 9. The biasing element female connector 280 and the biasing element male connector 290 are only exemplary and it is understood that any mating connector elements can be utilized to provide a releasable connection between the elongated biasing element 272 and the waist strap 210.

The biasing element female connector 280 includes a biasing element female connector body 281 having features to provide function thereof. A biasing element female connector receptacle 282 is formed between a first outer panel and a second outer panel. A distance between the first outer panel and the second outer panel is slightly greater than a thickness of an inserting portion of the biasing element male connector 290. A biasing element female connector latching edge 283 is provided at an interior end of each sidewall of the biasing element female connector receptacle 282. A biasing element female connector receptacle distal end 284 is provided at an interior end of the biasing element female connector receptacle 282. A biasing element female connector release enabling clearance 285 is formed along each side of the biasing element female connector body 281, wherein the biasing element female connector release enabling clearance 285 provides access to a biasing element male connector latching element 295, enabling the user to release engagement between the biasing element female connector 280 and the biasing element male connector 290. The biasing element female connector strap passage aperture 286 is formed through the biasing element female connector body 281 at a location proximate an attachment end of the biasing element female connector 280. The biasing element female connector strap passage aperture 286 creates the biasing element female connector strap attachment bar 287. A section of the biasing element connector strap 271 is inserted through the biasing element female connector strap passage aperture 286 forming the biasing element connector, connector attachment strap portion 275, and wrapped around the biasing element female connector strap attachment bar 287. The end of the biasing element connector, connector attachment strap portion 275 is secured to the biasing element connector strap 271 or the waist strap 210, securing the biasing element female connector 280 to the biasing element connector strap 271.

The biasing element male connector 290 includes a biasing element male connector body 291 having features to provide function thereof. A biasing element male connector latching element 295 is flexibly connected to a primary body by a biasing element male connector latching element flex member 294. The biasing element male connector strap passage aperture 296 is formed through the biasing element male connector body 291 at a location proximate an attachment end of the biasing element male connector 290. The biasing element male connector strap passage aperture 296 creates the biasing element male connector strap attachment bar 297. The biasing element male connector 290 is assembled to the elongated biasing element 272 by passing the elongated biasing element 272 through the biasing element male connector strap passage aperture 296 of the biasing element male connector 290. An elongated biasing element length adjusting buckle securing formation tail 274 is formed about the biasing element male connector strap attachment bar 297. The forward section and the rear section of the elongated biasing element 272 are retained at a desired length by the biasing element length adjusting buckle 240 as previously described.

A biasing element male connector central element 292 extends from the primary body, preferably along a central longitudinal axis. The biasing element male connector central element 292 is of a size and shape to limit an inward or compression motion of each biasing element male connector latching element 295. When a compression or releasing force is applied to each of the biasing element male connector latching element 295, motion of each biasing element male connector latching element 295 is limited when an interior surface of the each biasing element male connector latching element 295 would abut a facing surface of the biasing element male connector central element 292. During a process of inserting the biasing element male connector 290 into the biasing element female connector receptacle 282 of the biasing element female connector 280, each biasing element male connector latching element 295 is drawn inward towards the biasing element male connector central element 292. The biasing element male connector 290 is inserted into the biasing element female connector receptacle 282 until each biasing element male connector latching edge 293 passes the respective biasing element female connector latching edge 283. At this position, the biasing element male connector latching element 295 returns to a normal, uncompressed position, engaging the biasing element male connector latching edge 293 upon the biasing element female connector latching edge 283. Engagement between the biasing element male connector latching edge 293 and the biasing element female connector latching edge 283 retains the biasing element male connector 290 within the biasing element female connector receptacle 282 of the biasing element female connector 280 until purposely released. A biasing element female connector proximal edge 288 of the biasing element female connector 280 can butt against a biasing element male connector adjoining stop 298 of the biasing element male connector 290. This would prevent the biasing element male connector 290 from moving in a direction further inward respective to the biasing element female connector 280, creating a possibility of the biasing element male connector latching edge 293 and biasing element female connector latching edge 283 to disengage from one another. The inclusion of the biasing element female connector 280 and the biasing element male connector 290 enables the user to connect and disconnect the waist strap 210 and the heel cup 250 respective to one another.

The exemplary illustration presents the biasing element female connector 280 being assembled to the waist strap 210 via the biasing element connector strap 271 and the biasing element male connector 290 is located at an upper end of the elongated biasing element 272. It is understood that the arrangement can be reversed, where the connector components 280, 290 can be arranged to connect a lower end of the elongated biasing element 272 to the heel cup 250.

The exemplary illustration presents the biasing element female connector 280 being assembled to the waist strap 210 via the biasing element connector strap 271 and the biasing element male connector 290 is located at an upper end of the elongated biasing element 272. It is also understood that the orientations of the connector components 280, 290 can be reversed. In the exemplary illustration, the biasing element female connector 280 is assembled to the waist strap 210 by the biasing element connector strap 271 and the biasing element male connector 290 is assembled to the elongated biasing element 272. In an alternative arrangement, the biasing element male connector 290 can be assembled to the waist strap 210 by the biasing element connector strap 271 and the biasing element female connector 280 can be assembled to the elongated biasing element 272. The elongated biasing element assembly 272 can include one of the female connector 280 or the male connector 290, and the mating connector 290, 280 of the one of the female connector 280 and the male connector 290 connected to one of the waist band 210 or the heel cup 250. This enables the user to position the waist band waist strap 210 upon the waistline 312 of the recovering patient 300 and the heel cup 250 upon the heel 328 of the injured leg 320 of the recovering patient 300 without interference of the elongated biasing element assembly 270. Once the user positions the waist band waist strap 210 upon the waistline 312 of the recovering patient 300 and the heel cup 250 upon the heel 328 of the injured leg 320 of the recovering patient 300, the user can then connect the biasing element female connector 280 and the biasing element male connector 290 to one another.

Although the illustration presents the biasing element female connector 280 being assembled to the waist strap 210, it is understood that the biasing element female connector 280 can be assembled to the heel cup 250 and the biasing element male connector 290 would be located at an opposite end of the elongated biasing element 272.

A plurality of elongated biasing element assemblies 170, 270 can be provided as a set. The plurality of elongated biasing element assemblies 170, 270 would comprise elongated biasing elements 172, 272 having different moduli of elasticity. This provides the recovering patient 300 with an ability to adjust a resistive force generated by the elongated biasing element assembly 170, 270.

An example of the hamstring support assembly 100 in use is presented in the illustrations of FIGS. 10 and 11. It is understood that the hamstring support assembly 200 would be used in the same manner as the hamstring support assembly 100 as illustrated. The hamstring support assembly 100 is shown in use on a recovering patient 300. The exemplary recovering patient 300 introduces a torso 310, a waistline 312, a gluteus maximus 314, an injured leg 320, and an uninjured leg 330. The injured leg 320 can be referred to as a diagnosed leg 320, wherein the diagnosed leg 320 is diagnosed as one of: (a) having a hamstring injury or (b) recovering from the hamstring injury. Anatomy of the injured leg 320 includes an upper limb 322 and a lower limb 324. A knee 325 of the injured leg 320 pivots the upper limb 322 of the injured leg 320 and the lower limb 324 of the injured leg 320 respective to one another. An injured hamstring 326 is located on a rear side of the upper limb 322 of the injured leg 320. A calf 327 of the injured leg 320 is located on a rear side of the lower limb 324 of the injured leg 320. A foot 329 of the injured leg 320 is located at a lower end of the lower limb 324 of the injured leg 320. Anatomy of the uninjured leg 330 includes a leg upper limb 332 and a leg lower limb 334. A knee 335 pivots the leg upper limb 332 and the leg lower limb 334 respective to one another. A foot 339 of the uninjured leg 330 is located at a lower end of the leg lower limb 334. The illustration in FIGS. 10 and 11 show a heel 338 of the foot 339 of the uninjured leg 330.

The hamstring support assembly 100 would be assembled, if required, by joining a first end of the elongated biasing element 172 to the waist strap 110 and a second end of the elongated biasing element 172 to the heel posterior end 159 of the heel cup 150. Details of these arrangements are provided above. It is understood that the method and configuration for joining the first end of the elongated biasing element 172 to the waist strap 110 and the second end of the elongated biasing element 172 to the heel cup 150 can vary and be accomplished using any suitable joining configuration and respective method thereof.

The waist strap 110 would be placed about a waistline 312 of a recovering patient 300. The waist strap 110 would be orientated positioning the waist strap tail section 111 over the gluteus maximus 314 of the recovering patient 300. The waist strap 110 would be preferably positioned where the elongated biasing element 172 is in alignment or substantially parallel with the leg. The heel cup 150 is placed upon a heel 328 of the injured leg 320.

The recovering patient 300 would bend the injured leg knee 325 to orient the injured leg lower limb 324 in a retracted or bent position of a natural gait, as illustrated in FIG. 10. A length of the elongated biasing element assembly 170 can be adjusted where the elongated biasing element 172 would be slightly taut or neutral when the injured leg lower limb 324 is positioned at a bent relation to the injured leg upper limb 322.

A right shoe 341 would be placed upon the injured leg foot 329, entrapping the heel cup 150 between the injured leg foot 329 of the recovering patient 300 and an interior of the right shoe 341. A mating left shoe 342 would be placed upon the foot 339 of the uninjured leg 330 to provide balance to the recovering patient 300 while walking, stretching, jogging, running, and the like.

As the recovering patient 300 walks, jogs, runs, or any other motion of the injured leg 320 between a retracted position of the injured leg lower limb 324 and an extended position of the injured leg lower limb 324, the elasticity of the elongated biasing element 172 provides support to the injured hamstring 326 of the recovering patient 300.

Figure 12:
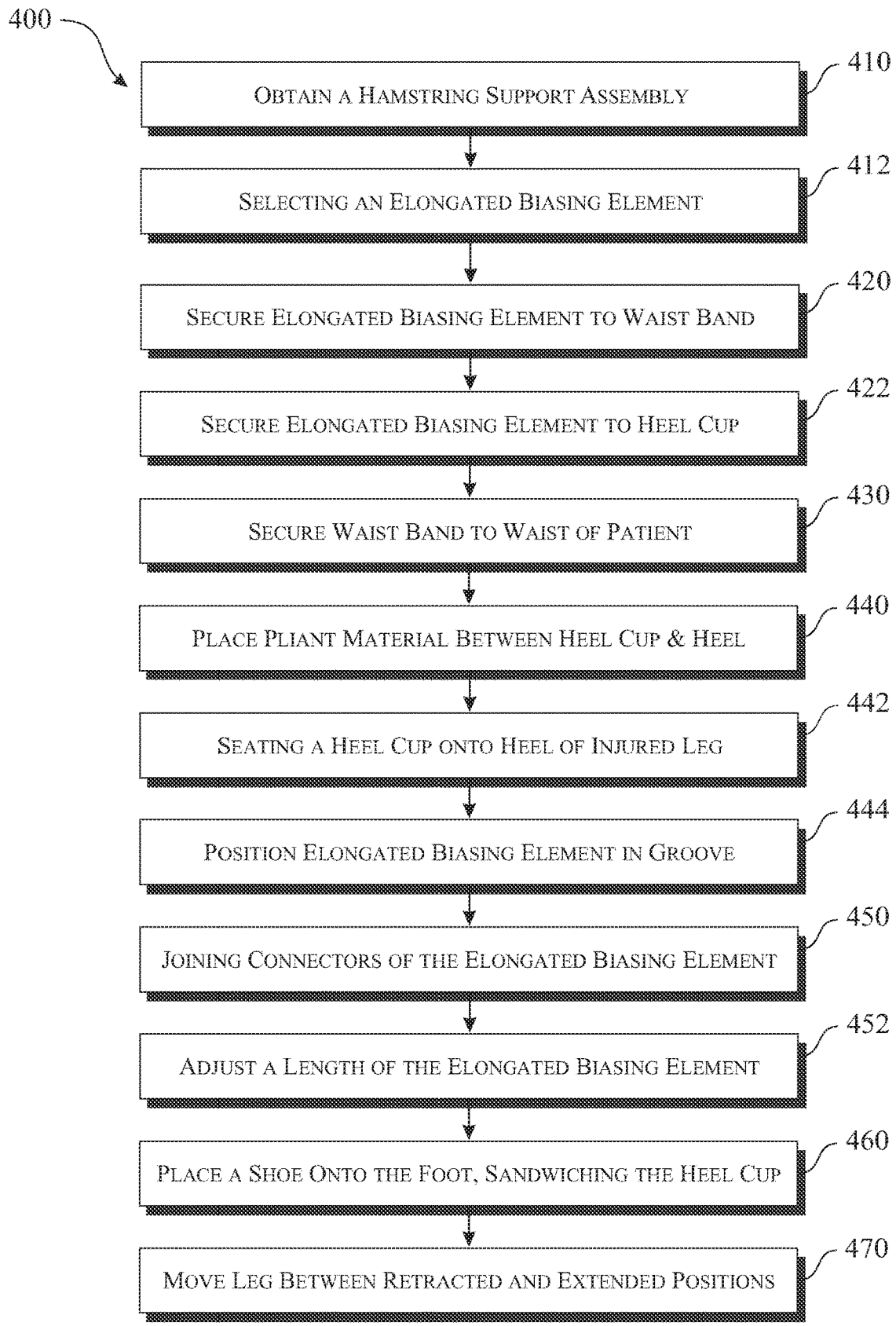
FIG. 12 presents an exemplary flow diagram providing steps of preparing and using the hamstring support assembly.

A method of using the hamstring support assembly 100, 200 is presented as a method of using a hamstring support assembly flow diagram 400 in FIG. 12. The method of use is initiated by a step of obtaining a hamstring support assembly 100, 200 (step 410). The patient can obtain the hamstring support assembly 100, 200 in either a preassembled configuration or as separate components, including a waist strap 110, 210; a heel cup 150, 250; and an elongated biasing element assembly 170, 270.

When the patient obtains the hamstring support assembly 100, 200 in the configuration having separate components, the components can include a plurality of elongated biasing element assemblies 170, 270 wherein two or more elongated biasing element assemblies 170, 270 would be of different spring constants or moduli of elasticity. This enables the patient to select an elongated biasing element assembly 170, 270 having a desired resistance suitable for the degree of support or treatment needed. When a plurality of elongated biasing element assemblies 170, 270 (or a plurality of elongated biasing elements 172, 272) are included, the patient, doctor, or any other party can select an elongated biasing element assembly 170, 270 (or an elongated biasing element 172, 272) having a desired spring constant or modulus of elasticity (step 412).

The process would continue by completing a step of securing the elongated biasing element assembly 170, 270 to the waist band 110, 210 (step 420). When the patient obtains the hamstring support assembly 100, 200 in the configuration having separate components, the process would continue by completing a step of securing the elongated biasing element assembly 170, 270 to the waist band 110, 210 (step 420). This can be accomplished using any known method of securing any elastic strap to a waist band. In the exemplary embodiments, an elongated biasing element 172 of an elongated biasing element assembly 170 is secured to the waist strap 110 by routing the elongated biasing element 172 through the waist band biasing element retention buckle 130 of the waist strap 110. In an alternative arrangement, the elongated biasing element 172 can be routed through an aperture formed through the waist strap 110, having a return portion directed back towards a forward portion of the elongated biasing element 172. The forward portion and the return portion of the elongated biasing element 172 would be secured to one another by any suitable means, including the exemplary heel cup biasing element retention buckle 140. An example of this arrangement is shown where the elongated biasing element 172 is secured to the heel cup 150 and the loop is referenced as the elongated biasing element heel cup securing formation 177.

Continuing the process in a condition where the patient obtains the hamstring support assembly 100, 200 in the configuration having separate components, the process continues with a step of securing the elongated biasing element assembly 170, 270 to the heel cup 150, 250 (step 422). Prior to the assembly step 422, the heel cup 150, 250 can be formed to the heel 328 of the injured patient 300 if the heel cup 150, 250 is fabricated of a suitable material. In this configuration, the heel cup 150, 250 would be heated to a temperature that is above ambient, but lower than a temperature that would injure the injured patient 300. This can be accomplished by placing the heel cup 150, 250 is a container of hot water; placing the heel cup 150, 250 into a standard oven, a microwave oven, a convection oven, a toaster oven, and the like; applying heat using a hair drier, a heat gun, and the like; or any other suitable method. Once the heel cup 150, 250 is heated to a suitable temperature, the heel cup 150, 250 would be placed against the heel 328 of the injured leg 320 of the injured patient 300 and formed to contour to the heel 328. The heel cup 150, 250 would then be allowed to cool, returning to a more rigid state, thus locking in the contoured shape. The elongated biasing element assembly 170, 270 would then be assembled to the heel cup 150, 250 in accordance with any suitable attachment method. This can include any of the attachment configurations described for securing the elongated biasing element assembly 170, 270 to the waist band 110, 210.

The process includes a step of securing the waist strap 110, 210 to a waistline 312 of the recovering patient 300 (step 430). This can be completed prior to a step of securing the elongated biasing element assembly 170, 270 to the waist strap 110, 210 or following a step of securing the elongated biasing element assembly 170, 270 to the waist strap 110, 210. The waist strap 110, 210 would be placed circumscribing the waistline 312 of the recovering patient 300. A first end of the waist strap 110, 210 and a second end of the waist strap 110, 210 would be joined together using any suitable joining interface. In the exemplary illustration, a first dense hook and loop tape segment 120 is provided proximate the first end of the waist strap 110, 210 and a second, mating dense hook and loop tape segment 122 is provided a first dense hook and loop tape segment 120 is provided proximate the second end of the waist strap 110, 210. The first dense hook and loop tape segment 120 and the second, mating dense hook and loop tape segment 122 are joined together, securing the waist strap 110, 210 upon the waistline 312 of the recovering patient 300.

When desired, a pliant material 166, 266 can be placed within the heel receiving cavity 152, 252 (step 440). This can cover at least one of: the heel cup heel (rear) panel 153, 253; the heel cup soul panel 156, 256, the heel cup right side panel 154, 254, and the heel cup left side panel 155, 255.

Continuing, the heel cup 150, 250 is seated upon the heel 328 associated with the injured leg 320 of the recovering patient 300 (step 442). This can be completed prior to a step of securing the elongated biasing element assembly 170, 270 to the heel cup 150, 250 or following a step of securing the elongated biasing element assembly 170, 270 to the heel cup 150, 250. In certain configurations, it may be preferred to complete this step following the step of securing the elongated biasing element assembly 170, 270 to the heel cup 150, 250.

With the heel cup 150, 250 seated upon the heel 328, the elongated biasing element 172, 272 of the elongated biasing element assembly 170, 270 can be positioned within the biasing element seating recess 164, 264 (step 444). The biasing element seating recess 164, 264 can be of any shape and size suitable for receiving and optionally partially encasing the elongated biasing element 172, 272 of the elongated biasing element assembly 170, 270.

In a configuration when the elongated biasing element assembly 270 includes at least one connector arrangement containing mating connector components 280, 290, mating components 280, 290 of the connector arrangement are joined to one another (step 450).

A length of the elongated biasing element assembly 170, 270 is adjusted to provide support to the injured hamstring 326 across a movement of the injured leg 320 of the recovering patient 300 between a retracted position (FIG. 10) and a fully extended position (FIG. 11) (step 452). This would be accomplished in a manner associated with the employed adjustment mechanism. For example, if a biasing element length adjusting buckle 240 is used, the elongated biasing element 272 would be positioned within the biasing element length adjusting buckle 240 to adjust a distance between the waist strap 110, 210 and the heel cup 150, 250.

A shoe 341 can be placed upon a foot 329 of the injured leg 320 of the recovering patient 300 (step 460). The heel cup 150, 250 would be sandwiched between an interior surface of the shoe 341 and the heel 328 of the injured leg 320 of the recovering patient 300.

Upon completion of the above steps, the recovering patient 300 would begin using the hamstring support assembly 100, 200 (step 470). The hamstring support assembly 100, 200 provides support to the injured hamstring 326 while walking, stretching, jogging, running, and the like. Details of the motion are presented in FIGS. 10 and 11 as described above.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

Element Description References

| Ref. No. | Description |
| --- | --- |
| 100 | hamstring support assembly |
| 110 | waist strap |
| 111 | waist strap tail section |
| 112 | waist strap first outer surface |
| 114 | waist strap second outer surface |
| 116 | waist strap elongated length |
| 117 | waist strap traversing height |
| 118 | waist strap support attachment tab horizontal dimension |
| 119 | waist strap attachment tab vertical height |
| 120 | first dense hook and loop tape segment |
| 122 | second, mating dense hook and loop tape segment |
| 130 | waist band biasing element retention buckle |
| 132 | waist band biasing element retention buckle frame |
| 134 | waist band biasing element retention buckle aperture surface |
| 136 | waist band biasing element retention buckle bar |
| 140 | heel cup biasing element retention buckle |

-continued

| Ref. No. | Description |
|---|---|
| 150 | heel cup |
| 151 | heel cup body |
| 152 | heel receiving cavity |
| 153 | heel cup heel (rear) panel |
| 154 | heel cup right side panel |
| 155 | heel cup left side panel |
| 156 | heel cup soul panel |
| 159 | heel posterior end |
| 160 | heel panel biasing element receiving aperture |
| 162 | sole panel biasing element receiving aperture |
| 164 | biasing element seating recess |
| 165 | biasing element seating recess sidewall |
| 166 | heel cup pliant material |
| 170 | elongated biasing element assembly |
| 172 | elongated biasing element |
| 173 | elongated biasing element waist securing formation |
| 174 | elongated biasing element waist securing formation tail |
| 177 | elongated biasing element heel cup securing formation |
| 178 | elongated biasing element heel cup securing formation tail |
| 200 | hamstring support assembly |
| 210 | waist strap |
| 211 | waist strap tail section |
| 212 | waist strap first outer surface |
| 214 | waist strap second outer surface |
| 220 | first dense hook and loop tape segment |
| 222 | second, mating dense hook and loop tape segment |
| 240 | biasing element length adjusting buckle |
| 250 | heel cup |
| 251 | heel cup body |
| 252 | heel receiving cavity |
| 253 | heel cup heel (rear) panel |
| 254 | heel cup right side panel |
| 255 | heel cup left side panel |
| 256 | heel cup soul panel |
| 259 | heel posterior end |
| 260 | heel panel biasing element receiving aperture |
| 262 | sole panel biasing element receiving aperture |
| 264 | biasing element seating recess |
| 266 | heel cup pliant material |
| 270 | elongated biasing element assembly |
| 271 | biasing element connector strap |
| 272 | elongated biasing element |
| 273 | elongated biasing element waist band buckle securing formation |
| 274 | elongated biasing element length adjusting buckle securing formation tail |
| 275 | biasing element connector, connector attachment strap portion |
| 276 | biasing element connector waist band attachment strap portion |
| 277 | elongated biasing element heel cup securing formation |
| 279 | elongated biasing element retention formation |
| 280 | biasing element female connector |
| 281 | biasing element female connector body |
| 282 | biasing element female connector receptacle |
| 283 | biasing element female connector latching edge |
| 284 | biasing element female connector receptacle distal end |
| 285 | biasing element female connector release enabling clearance |
| 286 | biasing element female connector strap passage aperture |
| 287 | biasing element female connector strap attachment bar |
| 288 | biasing element female connector proximal edge |
| 290 | biasing element male connector |
| 291 | biasing element male connector body |
| 292 | biasing element male connector central element |
| 293 | biasing element male connector latching edge |
| 294 | biasing element male connector latching element flex member |
| 295 | biasing element male connector latching element |
| 296 | biasing element male connector strap passage aperture |
| 297 | biasing element male connector strap attachment bar |
| 298 | biasing element male connector adjoining stop |
| 300 | recovering patient |
| 310 | torso |
| 312 | waistline |
| 314 | gluteus maximus |
| 320 | injured leg |
| 322 | upper limb of injured leg |
| 324 | lower limb of injured leg |
| 325 | knee of injured leg |
| 326 | injured hamstring |
| 327 | calf of injured leg |
| 328 | heel of injured leg |
| 329 | foot of injured leg |
| 330 | uninjured leg |
| 332 | leg upper limb |
| 334 | leg lower limb |
| 335 | knee |
| 338 | heel |
| 339 | foot |
| 341 | right shoe |
| 342 | left shoe |
| 400 | method of using a hamstring support assembly flow diagram |
| 410 | obtain a hamstring support assembly step |
| 412 | selecting an elongated biasing element step |
| 420 | secure an elongated biasing element to the waist band step |
| 422 | secure an elongated biasing element to the heel cup step |
| 430 | secure the waist band to a waist of patient step |
| 440 | place a pliant material between the heel cup and the heel step |
| 442 | seating the heel cup onto a heel of an injured leg step |
| 444 | position the elongated biasing element within an elongated biasing element receiving groove step |
| 450 | joining connectors of the elongated biasing element step |
| 452 | adjust a length of the elongated biasing element step |
| 460 | place a shoe onto the foot, sandwiching the heel cup between the foot and the heel step |
| 470 | move the injured leg between a retracted position and an extended position step |

What is claimed is:

1. A method of supporting a hamstring recovering from an injury, the method comprising steps of:

securing a waist band of a hamstring support assembly to a waist of a patient, the hamstring support assembly comprising:

the waist band, a heel cup fabricated of a rigid material having a fixed shape comprising a sole panel and a heel panel, wherein an interior surface of the sole panel and an interior surface of the heel panel define a heel receiving cavity, and an elongated biasing element assembly extending linearly between the waist band and a posterior end of the heel cup;

seating the heel cup to a heel of a patient by placing the heel within the heel receiving cavity, wherein the heel is a portion of a foot of a diagnosed leg, wherein the diagnosed leg is diagnosed as one of: (a) having a hamstring injury or (b) recovering from the hamstring injury;

adjusting a length of the elongated biasing element assembly such that the elongated biasing element of the elongated biasing element assembly is in one of having a slight tension or having a neutral tension when the diagnosed leg of the patient is fully extended; and moving the leg of the patient having the injured hamstring between a position where a knee of the diagnosed leg of the patient is straight and a position where the knee of the diagnosed leg is bent, providing a resistance to the movement of the leg of the patient via the elongated biasing element assembly in a linear direction extending directly between the waistband of the patient and the heel of the patient; and retaining a lateral motion of the heel cup respective to the heel using the rigidity and shape of the heel cup.

2. A method of supporting a hamstring recovering from an injury as recited in claim 1, the elongated biasing element assembly being provided as a plurality of elongated biasing element assemblies where at least one elongated biasing element of one elongated biasing element assembly and at least one second elongated biasing element of a second elongated biasing element assembly of the a plurality of elongated biasing element assemblies have different moduli of elasticity, the method further comprising steps of:

selecting one elongated biasing element having a modulus of elasticity to provide a desired level of support to the diagnosed leg from the plurality of elongated biasing elements; and assembling the selected elongated biasing element having a modulus of elasticity to provide a desired level of support to the diagnosed leg between the waist band and the heel cup.

3. A method of supporting a hamstring recovering from an injury as recited in claim 1, the shape of the heel cup further comprising a left side panel and a right side panel, wherein an interior surface of the left side panel and an interior surface of the right side panel are further included in defining the heel receiving cavity, the method further comprising a step of:

retaining the lateral motion of the heel cup respective to the heel by seating the heel against the interior surface of the left side panel and the interior surface of the right side panel.

4. A method of supporting a hamstring recovering from an injury as recited in claim 1, the method further comprising a step of:

placing a shoe onto the foot of the diagnosed leg, wherein the shoe sandwiches the sole panel and at least a portion of the heel panel between the shoe and the foot of the diagnosed leg.

5. A method of supporting a hamstring recovering from an injury as recited in claim 1, the elongated biasing element assembly further comprising an elongated biasing element, the heel cup further comprising a biasing element seating recess, the method further comprising a step of:

positioning the elongated biasing element within the biasing element seating recess.

6. A method of supporting a hamstring recovering from an injury as recited in claim 1, the elongated biasing element assembly further comprising an elongated biasing element, the method further comprising a step of:

positioning the waist band about the waist of the patient such to arrange the elongated biasing element to be substantially parallel to the diagnosed leg.

7. A method of supporting a hamstring recovering from an injury as recited in claim 1, the method further comprising a step of:

placing a pliant material between a body of the heel cup and the heel.

8. A method of supporting a hamstring recovering from an injury as recited in claim 1, the heel cup further comprising at least one of: a heel panel biasing element receiving aperture formed through the heel panel and a sole panel biasing element receiving aperture formed through the sole panel, the method further comprising a step of:

assembling the elongated biasing element assembly to one of the heel panel biasing element receiving aperture and the sole panel biasing element receiving aperture.

9. A method of supporting a hamstring recovering from an injury as recited in claim 1, the elongated biasing element assembly further comprising one of a male connector or a female connector, and a mating connector of the one of the male connector and a female connector connected to one of the waist band or the heel cup, the method further comprising a step of:

connecting the one of the male connector or the female connector to the mating connector of the one of the male connector and a female connector.

10. A method of supporting a hamstring recovering from an injury as recited in claim 1, wherein the heel cup is fabricated of a material that transitions from the rigid state to a moldable state when elevated in temperature to a temperature that is above ambient temperature, the method further comprising steps of:

elevating a temperature of the heel cup to a temperature above ambient, where the material of the heel cup becomes moldable; and molding the heel cup against the heel of the injured leg of the patient.

11. A method of supporting a hamstring recovering from an injury, the method comprising steps of:

securing a waist band to a waist of a patient, the patient comprising a diagnosed leg, wherein the diagnosed leg is diagnosed as one of: (a) having a hamstring injury or (b) recovering from the hamstring injury;

securing an elongated biasing element to a posterior end of a heel cup, the heel cup fabricated of a rigid material having a fixed shape comprising a sole panel and a heel panel, wherein an interior surface of the sole panel and an interior surface of the heel panel define a heel receiving cavity, the elongated biasing element assembly extending linearly between the waist band and the posterior end of the heel cup;

seating the heel cup to a heel of a patient by placing the heel within the heel receiving cavity, wherein the heel is a portion of a foot of the diagnosed leg;

securing the elongated biasing element to the waist band;

adjusting a length of the elongated biasing element such that the elongated biasing element is in one of having a slight tension or having a neutral tension when the diagnosed leg of the patient is fully extended; and moving the leg of the patient having the injured hamstring between a position where a knee of the diagnosed leg of the patient is straight and a position where the knee of the diagnosed leg is bent, providing a resistance to the movement of the leg of the patient via the elongated biasing element assembly in a linear direction extending directly between the waistband of the patient and the heel of the patient; and retaining a lateral motion of the heel cup respective to the heel using the rigidity and shape of the heel cup.

12. A method of supporting a hamstring recovering from an injury as recited in claim 11, the elongated biasing element being provided as a plurality of elongated biasing elements where at least one elongated biasing element of the plurality of elongated biasing elements and at least one second elongated biasing element of the plurality of elongated biasing elements have different moduli of elasticity, the method further comprising steps of:

selecting one elongated biasing element having a modulus of elasticity to provide a desired level of support to the diagnosed leg from the plurality of elongated biasing elements; and assembling the selected elongated biasing element having a modulus of elasticity to provide a desired level of support to the diagnosed leg between the waist band and the heel cup.

13. A method of supporting a hamstring recovering from an injury as recited in claim 11, the shape of the heel cup further comprising a left side panel and a right side panel, wherein an interior surface of the left side panel and an interior surface of the right side panel are further included in defining the heel receiving cavity, the method further comprising a step of:

retaining the lateral motion of the heel cup respective to the heel by seating the heel against the interior surface of the left side panel and the interior surface of the right side panel.

14. A method of supporting a hamstring recovering from an injury as recited in claim 11, the method further comprising a step of:

placing a shoe onto the foot of the diagnosed leg, wherein the shoe sandwiches the sole panel and at least a portion of the heel panel between the shoe and the foot of the diagnosed leg.

15. A method of supporting a hamstring recovering from an injury as recited in claim 11, the heel cup further comprising a biasing element seating recess, the method further comprising a step of:

positioning the elongated biasing element within the biasing element seating recess.

16. A method of supporting a hamstring recovering from an injury as recited in claim 11, the method further comprising a step of:

positioning the waist band about the waist of the patient such to arrange the elongated biasing element to be substantially parallel to the diagnosed leg.

17. A method of supporting a hamstring recovering from an injury as recited in claim 11, the method further comprising a step of:

placing a pliant material between a body of the heel cup and the heel.

18. A method of supporting a hamstring recovering from an injury as recited in claim 11, the heel cup further comprising at least one of: a heel panel biasing element receiving aperture formed through the heel panel and a sole panel biasing element receiving aperture formed through the sole panel, the method further comprising a step of:

assembling the elongated biasing element to one of the heel panel biasing element receiving aperture and the sole panel biasing element receiving aperture.

19. A method of supporting a hamstring recovering from an injury as recited in claim 11, the elongated biasing element further comprising one of a male connector or a female connector, and a mating connector of the one of the male connector and a female connector connected to one of the waist band or the heel cup, the method further comprising a step of:

connecting the one of the male connector or the female connector to the mating connector of the one of the male connector and a female connector.

20. A method of supporting a hamstring recovering from an injury as recited in claim 11, wherein the heel cup is fabricated of a material that transitions from the rigid state to a moldable state when elevated in temperature to a temperature that is above ambient temperature, the method further comprising steps of:

elevating a temperature of the heel cup to a temperature above ambient, where the material of the heel cup becomes moldable; and molding the heel cup against the heel of the injured leg of the patient.

* * * * *